(12) United States Patent
El-Gewely

(10) Patent No.: US 8,304,211 B2
(45) Date of Patent: *Nov. 6, 2012

(54) METHODS OF SCREENING MOLECULAR LIBRARIES AND ACTIVE MOLECULES IDENTIFIED THEREBY

(75) Inventor: Mohamed Raafat El-Gewely, Tomasjord (NO)

(73) Assignee: Mohamed Raafat El-Gewely, Tomasjord (NO)

( * ) Notice: Subject to any disclaimer, the term of this patent is extended or adjusted under 35 U.S.C. 154(b) by 0 days.

This patent is subject to a terminal disclaimer.

(21) Appl. No.: 13/043,284

(22) Filed: Mar. 8, 2011

(65) Prior Publication Data

US 2011/0294212 A1    Dec. 1, 2011

Related U.S. Application Data

(63) Continuation of application No. 10/502,510, filed as application No. PCT/GB03/00291 on Jan. 23, 2003, now abandoned.

(30) Foreign Application Priority Data

Jan. 23, 2002 (GB) .................................. 0201522.0
Jan. 23, 2002 (GB) .................................. 0201523.8

(51) Int. Cl.
  *C12P 21/06*    (2006.01)
(52) U.S. Cl. ........................................ 435/69.1; 435/375
(58) Field of Classification Search .................... None
See application file for complete search history.

(56) References Cited

U.S. PATENT DOCUMENTS

| | | | |
|---|---|---|---|
| 5,767,336 A | | 6/1998 | Skarnes |
| 6,110,889 A | * | 8/2000 | Miller et al. .................. 514/19.4 |
| 6,169,073 B1 | | 1/2001 | Halazonetis et al. |
| 6,180,343 B1 | | 1/2001 | Anderson et al. |
| 6,420,118 B1 | * | 7/2002 | Halazonetis et al. ........ 435/6.14 |
| 6,821,728 B1 | | 11/2004 | Escher et al. |
| 6,875,741 B2 | | 4/2005 | Pillutla et al. |
| 7,297,482 B2 | | 11/2007 | Anderson et al. |
| 2007/0128657 A1 | | 6/2007 | El-Gewely |

FOREIGN PATENT DOCUMENTS

EP    0989136 A1    3/2000

(Continued)

OTHER PUBLICATIONS

Palu et al., In pursuit of new developments for gene therapy of human diseases, Journal of Biotechnology 68 (1999) 1-13.*

(Continued)

*Primary Examiner* — James Ketter
*Assistant Examiner* — Reza Ghafoorian
(74) *Attorney, Agent, or Firm* — McDonnell Boehnen Hullbert & Berghoff LLP

(57) ABSTRACT

The present invention provides a peptide having 2 to 10 amino acids or a derivative thereof which is able to restore wild type function of human p53, for use in therapy; and a method of screening a library of molecules for the ability of members of that library to restore or modify the function of a target protein in an intra-cellular environment, which method comprises introducing the library into host cells which have a reporter system which allows the identification of those cells in which the function of the target protein has been restored or modified.

6 Claims, 15 Drawing Sheets

FOREIGN PATENT DOCUMENTS

| | | |
|---|---|---|
| WO | WO 97/14797 | 4/1997 |
| WO | WO 97/27212 | 7/1997 |
| WO | WO 98/13513 | 4/1998 |
| WO | WO 98/54210 | 12/1998 |
| WO | WO 99/067375 | 12/1999 |
| WO | WO 00/11216 | 3/2000 |

OTHER PUBLICATIONS

Selivanova et al., Reactivation of mutant p53 through interaction of a C-terminal peptide with the core domain, Mol Cell Biol. May 1999;19(5):3395-402.*

Hortsberg et al., The p53 Mutation HandBook, available online; http://p53.free.fr, last updated 2008.*

Friedler et al., A peptide that binds and stabilizes p53 core domain: Chaperone strategy for rescue of oncogenic mutants, PNAS, Jan. 22, 2002, vol. 99, No. 2, 937-942.*

Stretch et al., Expression of Mutant p53 in Melanoma, Cancer Research 51, 5976-5979. Nov. 1, 1991.*

Wolff, Ra, et al., A rapid and easy method for DNA recovery from agarose gels using Wizard minicolumns, Trends Genet, 12:339-340 (1996).

Daniels, et al., The characterization of p53 binding phage isolated from phage peptide display libraries, J. Mol. Biol. vol. 243:639-652 (1994).

Bullock, et al., *Quantitative analysis of residual folding and DNA binding in mutant p53 core domain: definition of mutant states for rescue in cancer therapy*, Oncogene, 19:1245-1256(2000).

Abarzua, et al., *Restoration of the transcription activation function to mutant p53 in human cancer cells*, Ocongene, 13:2477-2482(1996).

Bullock, et al., *Rescuing the Function of Mutant p53*, Nature, 1:68-76 (2001).

Blin, N., et al., *A general method for isolation of high molecular weight DNA from Eukaryotes*, Nucleic Acids Research, 3:2303-2308 (1976).

Colas, P., et al., *Genetic selection of peptide aptamers that recognize and inhibit cyclin-dependent kinase 2*, Nature, 380:548-550 (1996).

Ei-Deiry, W.S., et al., WAF1, *a potential mediator of p53 tumor suppression*, Cell, 75:817-825 (1993).

Ei-Gewely, M.R., *Shorter is better*, Nature Biotechnology, 17:210 (1999).

Fenton, C., et al., *Modulation of the Escherichia coli Tryptophan Repressor Protein by Engineered Peptides*, Biochem. Biophys. Res. Commun. 242:71-78 (1998).

Fukazawa, T., et al, *Differential involvement of the CD95 (Fas/APO-1) receptor/ligand system on apoptosis included by the wild-type p53 gene transfer in human cancer cells*, Oncogene, 18:2189-2199 (1999).

Gates, C.M., et al., *Affinity Selective Isolation of Ligands from Peptide Libraries through Display on a lac Repressor "Headpiece Dimer"*, J. Mol. Biol., 255:373-386 (1996).

Hanes, J., et al., *In vitro selection and evolution of functional proteins by using ribosome display.*, Proc. Natl. Acad. Sci. USA, 94:4937-4942 (1997).

Harayama, S., et al., *Artificial evolution by DNA shuffling*, Trends Biotechnol. 16:76-82 (1998).

Hermeking, H., et al., *14-3-3 sigma is a p53-regulated inhibitor of G2/M progression*, Mol. Cell., 1:3-11 (1997).

Kim, Al., et al., *Conformational and Molecular Basis for Induction of Apoptosis by a p53 C-terminal Peptide in Human Cancer Cells*, J. Biol. Chem. 274:34924-34931 (1999).

Lowman, H.B., *Bacteriophage Display and Discovery of Peptide Leads for Drug Development*, Annu. Rev. Biophys Biol. Struct., 26:401-424 (1997).

Parker, B.A., et al., *Regulation of simian virus 40 transcription: sensitive analysis of the RNA species present early in infections by virus or viral DNA*, J. Virol. 31:360-369 (1979).

Sigal, A., et al., *Oncogenic Mutations of the p53 Tumor Suppressor: The Demons of the Guardian of the Genome*, Cancer Res., 60:6788-6793 (2000).

Storbakk, N., et al., *In vivo Interaction Between Mutated Tryptophan Repressors of Eschericia coli*, Journal of Molecular Biology, 256:889-896(1996).

Thornborrow, E.C., et al., *One Mechanism for Cell Type-specific Regulation of the bax Promoter by the Tumor Suppressor p53 is Dictated by the p53 Response Element*, J. Biol. Chem., 274:33747-33756, (1999).

Varshaysky, A., *The N-end rule pathway of protein degradation*, Genes to Cells, 2:13-28 (1997).

Vogelstein, B., et al., *Surfing the p53 network*, Nature, 408:307-310 (2000).

Watanabe, T., et al., *Induction of wild-type p53 activity in human cancer cells by ribozymes that repair mutant p53 transcripts*, Proc. Natl. Acad. Sci., 97:8490-8494 (2000).

Xu, H., et al., *P53-responsive genes and the potential for cancer diagnostics and therapeutics development.* Biotechnology Annual Review, Elsevier Science B.V., 7:131-164 (2001).

Yu, J., et al., *Identification and classification of p53-regulated genes*, Proc. Natl. Acad. Sci. 96:14517-14522 (1999).

Famulok, M., et al., *Nucleic Acid Aptamers—From Selection in Vitro to Applications in vivo*, Acc. Chem. Res., 33:591-599 (2000).

Hermann, T., et al., *Adaptive Recognition by Nucleic Acid Aptamers*, Science, 287:820-825 (2000).

Hicke, BJ., et al., *Tenascin-C Aptamers Generated Using Tumor Cells and Purified Protein*, J. Biol. Chem., 276:48644-58654 (2001).

Hoppe-Seyler, F., et al., *Peptide aptamers: new tools to study protein interactions*, J. Steroid Biochem Mol. Biol., 78:105-111(2001).

Jayasena, S.D., *Aptamers: An Emerging Class of Molecules That Rival Antibodies in Diagnostics*, Clin Chem., 45:1628-1650 (1999).

Gold, et al., *From oligonucleotide shapes to genomic SELEX: Novel biological regulatory loops*, Proc. Natl. Acad. Sci., 94:59-64 (1997).

Ellington, et al., *Aptamers as potential nucleic acid pharmaceuticals*, Biotechnology Annual Review, Elsevier Science B.V., 1:185-214 (1995).

Takimoto, et al., *The Mutant p53-Conformation Modifying Drug, CP-31398, Can Induce Apoptosis of Human Cancer Cells and Can Stabilize Wild-Type p53 Protein*, Cancer Biology & Therapy, 1:47-55 (2002).

Foster, et al., *"Pharmacological Rescue of Mutant p53 Conformation and Function"*, Science, vol. 286:2507-2510 (1999).

Geyer, et al., *"Mutagenesis" by Peptide Aptamers Identifies Genetic Network Members and Pathway Connections*, Genetics, vol. 96:8567-8562 (1999).

Phizicky, et al., *"Protein-Protein Interactions: Methods for Detection of Analysis"*, Microbiological reviews, vol. 59:94-123 (1995).

Selivanova, et al., *"Restoration of the growth Suppression Function of Mutant p53 by a Synthetic Peptide derived from the p53 C-terminal Domain"*, Nature Medicine, vol. 3:632-638 (1997).

Tenson, et al., *"Erthromycin Resistance Peptides Selected from Random Peptide Libraries"*, Journal of Biological Chemistry, vol. 272:17425-17430 (1997).

Tenson, et al., *"Inhibition of translation and Cell Growth by Minigene Expression"*, Journal of Bacteriology, vol. 181:1617-1622 (1999).

Tripathi, et al., *"Ketolide Resistance Conferred by Short Paptides"*, Journal of Biological Chemistry, vol. 273:10073-20077 (1998).

Yang, et al., *"Protein-Peptide Interactions Analyzed with yeast Two-hybrid System"*, Nucleic Acids research, vol. 23:1152-1156 (1995).

* cited by examiner

SEQUENCE LISTING

```
<160> NUMBER OF SEQ ID NOS: 53

<210> SEQ ID NO 1
<211> LENGTH: 21
<212> TYPE: PRT
<213> ORGANISM: Artificial Sequence
<220> FEATURE:
<223> OTHER INFORMATION: secretion signal peptide

<400> SEQUENCE: 1

Met Glu Thr Asp Thr Leu Leu Leu Trp Val Leu Leu Leu Trp Val Pro
1               5                   10                  15

Gly Ser Thr Gly Asp
            20

<210> SEQ ID NO 2
<211> LENGTH: 49
<212> TYPE: PRT
<213> ORGANISM: Artificial Sequence
<220> FEATURE:
<223> OTHER INFORMATION: transmembrane domain

<400> SEQUENCE: 2

Ala Val Gly Gln Asp Thr Gln Glu Val Ile Val Val Pro His Ser Leu
1               5                   10                  15

Pro Phe Lys Val Val Val Ile Ser Ala Ile Leu Ala Leu Val Val Leu
            20                  25                  30

Thr Ile Ile Ser Leu Ile Ile Leu Ile Met Leu Trp Gln Lys Lys Pro
        35                  40                  45

Arg

<210> SEQ ID NO 3
<211> LENGTH: 5
<212> TYPE: PRT
<213> ORGANISM: Artificial Sequence
<220> FEATURE:
<223> OTHER INFORMATION: peptide derivative

<400> SEQUENCE: 3

Met Gly Trp Cys Thr
1               5

<210> SEQ ID NO 4
<211> LENGTH: 190
```

```
<212> TYPE: DNA
<213> ORGANISM: Artificial Sequence
<220> FEATURE:
<223> OTHER INFORMATION: vector

<400> SEQUENCE: 4
ttgacgcaaa tgggcggtag gcgtgtacgg tgggaggtct atataagcag agctcgttta      60
gtgaaccgtc agatctctag aagctgggta ccagctgcta gcaagcttgc tagcggccgc     120
tcgaggccgg caaggccgga tccagacatg ataagataca ttgatgagtt tggacaaacc     180
acaactagaa                                                             190

<210> SEQ ID NO 5
<211> LENGTH: 70
<212> TYPE: DNA
<213> ORGANISM: Artificial Sequence
<220> FEATURE:
<223> OTHER INFORMATION: vector
<220> FEATURE:
<221> NAME/KEY: misc_feature
<223> OTHER INFORMATION: N = A, C, G or T in equal molar ratio
<220> FEATURE:
<221> NAME/KEY: misc_feature
<223> OTHER INFORMATION: K = G or T in equal molar ratio
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (39)..(39)
<223> OTHER INFORMATION: K = G or T in equal molar ratio
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (42)..(42)
<223> OTHER INFORMATION: K = G or T in equal molar ratio
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (45)..(45)
<223> OTHER INFORMATION: K = G or T in equal molar ratio

<400> SEQUENCE: 5
aagagctcgg taccaagaag gagtttacat atgggannkn nknnktgata aggatccaag      60
cttgaattca                                                             70

<210> SEQ ID NO 6
<211> LENGTH: 23
<212> TYPE: DNA
<213> ORGANISM: Artificial Sequence
<220> FEATURE:
<223> OTHER INFORMATION: synthetic sequence

<400> SEQUENCE: 6
aagagctcgg taccaagaag gag                                              23

<210> SEQ ID NO 7
<211> LENGTH: 25
<212> TYPE: DNA
<213> ORGANISM: Artificial Sequence
<220> FEATURE:
<223> OTHER INFORMATION: synthetic sequence

<400> SEQUENCE: 7
```

```
ctgaattcaa gcttggatcc ttatc                                          25

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
agagctcgtt tagtgaaccg                                                20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gtggtttgtc caaactcatc                                                20

<210> SEQ ID NO 10
<211> LENGTH: 55
<212> TYPE: DNA
<213> ORGANISM: Artificial Sequence
<220> FEATURE:
<223> OTHER INFORMATION: library sequence

<400> SEQUENCE: 10
ggtaccaaga aggagtttac atatgggatg gtgtacttga taaggatcca agctt         55

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ctacctcagg cagctcaagc                                                20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
agacagcacc ctcatcatgc                                                20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
tggtgctcat cttaatggcc                                                20

<210> SEQ ID NO 14
<211> LENGTH: 20
<212> TYPE: DNA
<213> ORGANISM: Artificial Sequence
```

```
<220> FEATURE:
<223> OTHER INFORMATION: primer

<400> SEQUENCE: 14
tgacaaaacc taacttgcgc                                           20

<210> SEQ ID NO 15
<211> LENGTH: 26
<212> TYPE: DNA
<213> ORGANISM: Artificial Sequence
<220> FEATURE:
<223> OTHER INFORMATION: Primer

<400> SEQUENCE: 15
aagcagtggt aacaacgcag agtact                                    26

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
aagcagtggt aacaacgcag agt                                       23

<210> SEQ ID NO 17
<211> LENGTH: 34
<212> TYPE: DNA
<213> ORGANISM: Artificial Sequence
<220> FEATURE:
<223> OTHER INFORMATION: Primer

<400> SEQUENCE: 17
atctaagctt gaggcttcag cccgggaatt ccag                           34

<210> SEQ ID NO 18
<211> LENGTH: 34
<212> TYPE: DNA
<213> ORGANISM: Artificial Sequence
<220> FEATURE:
<223> OTHER INFORMATION: Primer

<400> SEQUENCE: 18
atctaccggt gccagcagtg gcgccgtcca acag                           34

<210> SEQ ID NO 19
<211> LENGTH: 31
<212> TYPE: DNA
<213> ORGANISM: Artificial Sequence
<220> FEATURE:
<223> OTHER INFORMATION: Primer

<400> SEQUENCE: 19
aataacccgg gtcgccacca tggtgagcaa g                              31

<210> SEQ ID NO 20
<211> LENGTH: 34
<212> TYPE: DNA
<213> ORGANISM: Artificial Sequence
<220> FEATURE:
<223> OTHER INFORMATION: Primer

<400> SEQUENCE: 20
aataatctag aacttgtaca gctcgtccat gccg                           34
```

```
<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
tcgtaaatca ctgcataatt cg                                             22

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
gtccataccc tttttacgtg aa                                             22

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
gattagcgga tcctacctga cg                                             22

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
gccaggcaaa ttctgtttta tc                                             22

<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
tcaggtcggg aattatcgca ttat                                           24

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
tcgccgtaat ggctagtcac atcc                                           24

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
```

```
taatacgact cactataggg                                               20

<210> SEQ ID NO 28
<211> LENGTH: 17
<212> TYPE: DNA
<213> ORGANISM: Artificial Sequence
<220> FEATURE:
<223> OTHER INFORMATION: Primer

<400> SEQUENCE: 28
attaaccctc actaaag                                                  17

<210> SEQ ID NO 29
<211> LENGTH: 24
<212> TYPE: DNA
<213> ORGANISM: Artificial Sequence
<220> FEATURE:
<223> OTHER INFORMATION: Primer

<400> SEQUENCE: 29
cgattacgcg tgaatctaac agcc                                          24

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
ggctgttaga ttcacgcgta atcg                                          24

<210> SEQ ID NO 31
<211> LENGTH: 25
<212> TYPE: DNA
<213> ORGANISM: Artificial Sequence
<220> FEATURE:
<223> OTHER INFORMATION: Primer

<400> SEQUENCE: 31
cctgatgctg atgccagatg agcgc                                         25

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
gcgctcatct ggcatcagca tcagg                                         25

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
gataatgtgc gcgtcgaata                                               20

<210> SEQ ID NO 34
<211> LENGTH: 20
<212> TYPE: DNA
<213> ORGANISM: Artificial Sequence
```

```
<220> FEATURE:
<223> OTHER INFORMATION: Primer

<400> SEQUENCE: 34
tttgcggaaa cgcagatcgt                                               20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
gtgtcgccct tattcccttt                                               20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
ggcacctctc tcagcgatct                                               20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
agcgaatacg tcttccgtca                                               20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
gatggctggt ttccatcagt                                               20

<210> SEQ ID NO 39
<211> LENGTH: 21
<212> TYPE: DNA
<213> ORGANISM: Artificial Sequence
<220> FEATURE:
<223> OTHER INFORMATION: library sequence

<400> SEQUENCE: 39
atgggttttt ggaggtgata a                                             21

<210> SEQ ID NO 40
<211> LENGTH: 5
<212> TYPE: PRT
<213> ORGANISM: Artificial Sequence
<220> FEATURE:
<223> OTHER INFORMATION: library sequence

<400> SEQUENCE: 40

Met Gly Phe Leu Arg
1               5
```

```
<210> SEQ ID NO 41
<211> LENGTH: 5
<212> TYPE: PRT
<213> ORGANISM: Artificial Sequence
<220> FEATURE:
<223> OTHER INFORMATION: library sequence

<400> SEQUENCE: 41

Met Gly Phe Trp Arg
1               5

<210> SEQ ID NO 42
<211> LENGTH: 71
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: N = A, T, G or C
<220> FEATURE:
<221> NAME/KEY: misc_feature
<223> OTHER INFORMATION: K = G or T
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (39)..(39)
<223> OTHER INFORMATION: K = G or T
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (42)..(42)
<223> OTHER INFORMATION: K = G or T
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (45)..(45)
<223> OTHER INFORMATION: K = G or T

<400> SEQUENCE: 42
aagagctcgg taccaagaag gagtttacat atgggannkn nknnktgata aggatccaag    60
cttgaattca g                                                         71

<210> SEQ ID NO 43
<211> LENGTH: 23
<212> TYPE: DNA
<213> ORGANISM: Artificial Sequence
<220> FEATURE:
<223> OTHER INFORMATION: Primer

<400> SEQUENCE: 43
aagagctcgg taccaagaag gag                                            23

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
ctgaattcaa gcttggatcc ttatc                                          25
```

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
agagctcgtt tagtgaaccg                                          20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gtggtttgtc caaactcatc                                          20

<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
aagagctcgg taccaagaag gag                                      23

<210> SEQ ID NO 48
<211> LENGTH: 25
<212> TYPE: DNA
<213> ORGANISM: Artificial Sequence
<220> FEATURE:
<223> OTHER INFORMATION: Primer

<400> SEQUENCE: 48
ctgaattcaa gcttggatcc ttatc                                    25

<210> SEQ ID NO 49
<211> LENGTH: 25
<212> TYPE: DNA
<213> ORGANISM: Artificial Sequence
<220> FEATURE:
<223> OTHER INFORMATION: library sequence

<400> SEQUENCE: 49
caagcttgct agcagctggt accca                                    25

<210> SEQ ID NO 50
<211> LENGTH: 84
<212> TYPE: DNA
<213> ORGANISM: Artificial Sequence
<220> FEATURE:
<223> OTHER INFORMATION: library sequence

<400> SEQUENCE: 50
cctcgagctg ccgctagcaa gcttggatcc ttatcaagta caccatccca tatgtaaact    60
ccttcttggt acccagcttc taga                                          84

<210> SEQ ID NO 51
<211> LENGTH: 5
<212> TYPE: PRT
<213> ORGANISM: Artificial Sequence

```
<220> FEATURE:
<223> OTHER INFORMATION: Peptide
<220> FEATURE:
<221> NAME/KEY: MISC_FEATURE
<222> LOCATION: (2)..(2)
<223> OTHER INFORMATION: Xaa = G or M or V

<400> SEQUENCE: 51

Met Xaa Trp Cys Thr
1               5

<210> SEQ ID NO 52
<211> LENGTH: 6
<212> TYPE: PRT
<213> ORGANISM: Artificial Sequence
<220> FEATURE:
<223> OTHER INFORMATION: peptide

<400> SEQUENCE: 52

Met Gly Trp Cys Thr Lys
1               5

<210> SEQ ID NO 53
<211> LENGTH: 4
<212> TYPE: PRT
<213> ORGANISM: Artificial Sequence
<220> FEATURE:
<223> OTHER INFORMATION: peptide

<400> SEQUENCE: 53

Trp Cys Thr Lys
1
```

METHODS OF SCREENING MOLECULAR LIBRARIES AND ACTIVE MOLECULES IDENTIFIED THEREBY

This application is a continuation of U.S. Ser. No. 10/502,510, filed May 2, 2005, which claims priority to international application PCT/GB03/00291, filed Jan. 23, 2003. These applications are herein incorporated by reference in their entirety.

The present invention relates to methods of screening molecular libraries, to the uses of molecules identified by such screening methods and to such molecules themselves.

Gene therapy has yet to establish itself as the technique of choice for treatment of genetic diseases and of cancers caused by genetic mutations. Despite the new wealth of genetic information, the initial enthusiasm about the potential for gene therapy has been dampened by practical problems encountered in providing on effective therapy for most diseases having a genetic cause. The basic principle of such gene therapy is that a nucleic acid construct which encodes a target protein in its wild type protein can be introduced into a patient's cells to counteract deficiencies in expression or mutations in the version of the target protein normally expressed by the patient. Thus, a patient receiving gene therapy will typically produce the recombinant wild type protein in addition to the defective protein encoded by their own genome.

A large number of genetic defects/diseases are known but from these only a limited gene-list for gene therapy candidates exists. Typically, in order to encode a whole protein, the corresponding gene/cDNA must be generated and introduced into the patient in order to express the encoded protein under the regulation of a suitable promoter. Large DNA sequences pose a very high risk of containing immunogenic sequences that can lead to adverse effects, especially with repeated administration of the gene/vector combinations. In addition, while the use of viral vectors for treating humans is undesirable, most current gene therapy trials have relied on viral-based vectors.

There is therefore a need for an alternative to gene therapy for treating genetic disorders, preferably a method which relies on the administration of a relatively simple molecule. Pharmaceutical companies and the medical profession have much expertise in the administration and production of small organic compounds, peptides, steroids etc. and therefore a range of suitable carriers and methods of administration are available once a compound is found to be effective.

Protein therapy has been proposed which involves the introduction of a replacement wild type protein but again, the administration of a whole protein, while possible with small proteins like insulin, is much more difficult when the deficient or mutant protein is large.

It has long been assumed that the primary structure of a protein, i.e. the amino acid sequence (which is in turn dependent on the nucleic acid coding sequence), determines the tertiary/quaternary structure of the protein (see, e.g. Anfinsen, C. (1986) Protein Engineering Ed. Inouye and Sarma pp 3-13). However, we have established a method that does not rely on replacement of the mutated gene, but rather aims at the correction of the protein expressed by the mutated gene. Thus, while the mutant protein may have an altered three-dimensional structure due to a non-wild type primary structure, the three-dimensional structure can be altered without correcting the primary structure. Preferably, small molecules, e.g. peptides or small organic molecules, may be used which interact with the mutant protein to modify its three dimensional structure and thus its activity. Proteins are known to change their conformation on binding or associating with a range of different classes of molecules, e.g. other proteins, nucleic acids, prosthetic groups such as heme, ions such as $Ca^{2+}$ etc.

It is now proposed to utilise small ligands to alter the three-dimensional structure of a mutant protein to restore or alter the function or activity of that mutant protein. Typically the ligand can restore, in whole or in part, wild type protein function. Protein function restoration is conveniently referred to herein as PFR. It could perhaps be attempted to design molecules, e.g. through computer modelling, which it is hoped would have the desired impact on the target mutant protein. However even with sophisticated modelling programs, it is still difficult to build in accurately all the possible conformational changes that could occur on ligand binding, particularly with a complicated protein. Moreover, it would still be necessary to test these candidate molecules for their activity in vitro/in vivo.

A solution to these problems is offered by the present invention, which according to one aspect provides a method of screening a library of molecules for the ability of members of that library to restore or modify the function of a target protein in an intra-cellular environment, which method comprises introducing the library into host cells which have a reporter system which allows the identification of those cells in which the function of the target protein has been restored or modified.

The library of molecules under investigation will typically be peptide molecules or other organic molecules, whether organically synthesised or natural products. Such libraries of organic compounds are now commercially available. Peptidomimetics which may have a peptide like backbone and functional groups appended thereto are a useful class of small organic molecules.

The term "peptide" is used herein to encompass molecules which might be termed "oligopeptides" or "polypeptides" by those in the art. It will be appreciated that where the members of the library having the ability to restore or modify protein functions are peptides, the peptide library may actually be introduced into the cells in the form of a library of nucleic acid molecules or constructs (preferably DNA plasmid vectors) which encode the peptide molecules to be screened and investigated. The 'genes' encoding the peptides can be expressed constitutively or expression can be induced from a specific promoter. Introduced nucleic acid constructs encoding the peptide library may be autonomously replicated or integrated into the host cell chromosome. This is, in fact, a particularly preferred way of performing the invention and is discussed in more detail below and in the Examples. Alternatively, a library of peptide molecules may be introduced directly as peptides, which have been expressed outside the cells having the reported system or chemically synthesised.

It has surprisingly been found that very small peptides can restore or modify the function of target proteins through interacting with them in vivo and causing changes in their conformation. The members of a peptide library therefore typically have no more than 12 amino acids, preferably 2-8 amino acids e.g. 4-6 amino acids. When a library of non-peptides molecules is analysed, they will generally be of comparable or even smaller size.

Because of the suitability of peptide/peptide interactions in promoting conformational changes, peptidomimetics are a preferred class of non-peptide molecules which may make up the library screened in accordance with a method of the invention. The design and production of peptidomimetics is now well known in the art and the skilled man is aware of how such molecules may be prepared and screened. Many pharmaceutical and other companies have their own banks of peptidomimetics and other organic compounds which could be used in the in vivo screening methods of the present invention. Examples of suppliers of compound libraries include Advanced Chemtech, Affymax, BioLeads GmbH, and ComGenex, Inc., etc.

We describe a method of "screening a library". While the library may have been selected or designed to have certain structural motifs and the nature of individual members of that library can be assumed, this phrase implies that it is not known which member is introduced into which cell (or cell sample) and the molecules are not introduced in a controlled series.

The library which is screened in accordance with the present invention will typically have at least 96 different members, which are usually screened at the same or substantially the same time, e.g. the library members are in contact with the host cells at the same time or at least screened as part of a series of coordinated multiplex assays. Preferably the library will comprise at least 500 different members (species) more preferably at least 1000, e.g. at least 5000, particularly preferably at least 10,000 or even at least 25,000 members.

The library may be screened all together or in batches but in that case at least 8, preferably at least 64 or 96 different library members would still be contacted with the host cell population at the same time.

A suitable protocol for screening chemical libraries would be to use cancer cells containing an engineered reporter/screening system. These cells are placed with a culture medium on microtitre plates, where one compound from the library is present in each well, thus non-peptide libraries may be screened in batches.

Non-peptide libraries or peptide libraries which are not encoded by mini-genes may be screened on an array. Chemical arrays having 500 eg 1,000 or more different compounds with each compound identified to a fixed address within that array are commercially available. The screening methods of the present invention are particularly effective in this regard as positive results are only obtained with molecules which can enter the cell, restore or modify target protein function and are non-toxic.

The method provided is a "screening method" in that performance of the method gives information about individual members of the library of molecules. The method is performed in an intra-cellular environment (i.e. in vivo), and therefore all toxic compounds will be weeded out very early on. This reduces the cost of screening and of pre-clinical and even phase I clinical trials. The method is able to indicate in a qualitative possibly also quantitative manner the performance of individual molecules in the test system. A target protein and suitable host cells are selected and the method designed so that the reporter system is able to give information about the ability of each molecule to restore or modify the function of the target protein. In preferred embodiments, the ability of members of the library to restore the function of the target protein is assessed although alternatively it may be useful to investigate the potential for modifying protein function.

Thus, when the function of the target protein has been "restored" a form of protein therapy has taken place which advantageously relies on administration of small modulating molecules rather than a full replacement protein (or a nucleic acid molecule encoding for the full protein). Restoration of function is determined in relation to the function, in a physiologically relevant respect, of the wild-type protein found in healthy cells. Mutant variants of proteins may exist in cells and contribute to various disease conditions, for example many cancers are caused by the presence in certain cells of the body of one or more mutant versions of naturally occurring proteins, e.g. proteins responsible for cell growth and the normal working of the cell cycle. Numerous other diseases are caused by the presence in cells of a mutant version of a naturally occurring protein, e.g. cystic fibrosis, sickle cell anaemia, phenylketonuria, multiple carboxylase deficiency, methylpurine DNA glycosylase deficiency (MPG), ataxia, chemotherapy resistance due to mutations in the gene coding for methylguanine-DNA methyl transferase (MGMT) etc.

The reporter system is typically designed to measure restoration of a particular function of the target protein, for example the ability to act as a DNA binding transcription factor. Thus restoration of function refers to a return to wild-type function of the protein in at least one physiologically relevant and measurable respect. In many cases, the wild-type functions of the target protein in all respects may be restored but this is not essential for the successful working of the invention. It will be appreciated that partial restoration of the function of a protein may still be useful and it is not a requirement for a positive identification according to the claimed screening method to provide return to 100% of wild-type activity.

The sensitivity of the reporter system may conveniently be modified to provide a more or less stringent assay and thus to identify as giving "positive" results only those molecules which have achieved a significant increase in protein function. Preferably, molecules giving positive results according to the claimed screening methods will have brought about at least a 30%, more preferably at least a 50%, particularly preferably at least a 70% restoration in wild-type protein function, with respect to the particular function monitored by the intra-cellular reporter system. In some instances, a ligand may correct the mutant to a level of measured activity which is actually better than wild type. It will be clear to the skilled reader that the art provides a number of ways of comparing the relative activities of different molecules. Some reporter systems e.g. those based on fluorescence may be quantitative and thus facilitate such a comparison between wild-type and corrected mutant. However an assessment relative to the wild-type protein may more conveniently be performed as part of a separate test utilising serial dilutions, measurement of plaque size etc.

Unless otherwise clear from the context, the above discussion also applies to the circumstance where a particular function/activity of a protein is modified. "Modification" of function refers to the situation where the function of a wild type protein in one or more physiologically relevant respects is altered, e.g. to enhance or decrease binding affinity for an enzyme's co-factor or substrate, or ability to promote gene expression through DNA binding.

Suitable target proteins for restoration of function will include those whose presence in mutated form is associated with a disease state. The mutated version of the protein will typically have an altered 3-dimensional structure which affects its ability to interact with other molecules (ions, intracellular organelles and other cell components etc.). The members of the molecular library will be screened for their ability to interact with the mutant target and thus alter its 3-dimensional structure. The 3-dimensional structure in vivo may be closer in one or more respects to the wild-type 3-dimensional structure as a result of successful interaction with a member of the library but protein function may be restored through a further compensating change in 3-dimensional structure which has a return to wild-type function as a 'net' result.

Preferred target proteins will be those wherein point mutation(s) are the cause of disease. Particularly preferred are transcription factors (DNA binding proteins) such as p53, but others would be enzymes, peptide hormones or receptor molecules. All diseases caused by monogenic Mendelian mutations could be targets for treatment with molecules identified according to the screening methods of the present invention. These include genetic (i.e. hereditary) diseases, cancer and symptoms of aging caused by mutations. Specific diseases such as MPG, MGMT etc. are listed above.

Key to the presently claimed screening methods is the fact that the library is screened in vivo, i.e. the influence of each molecule within an intra-cellular environment is monitored. This offers considerable advantage over in vitro methods of screening lead compounds such as those using phage display, for example, which relies on binding/screening taking place outside the phage. Phage display is further limited in that putative binding ligands are expressed as an integral part of a phage surface protein. In a preferred embodiment of the present invention, the library of molecules is introduced into the host cells in the form of expression vectors, e.g. plasmids or bacteriophage vectors which express the peptides to be screened freely, without the need to conjugate with an existing cellular protein. The screened peptides are small, as discussed above, typically comprising no more than 12 amino acids, although they may initially be translated as a fusion protein with a cleavable signal sequence.

Suitable host cells are chosen which are capable of expressing the target protein. Preferably the host cells are eukaryotic, more particular of human origin, although it may be desired to manipulate a prokaryotic, e.g. bacterial protein in which case prokaryotic host cells will be used. The host cells should provide a suitable model for determining whether the members of the library are capable of causing the desired change in target protein function with a view, typically, to therapeutic administration of successful members of the library or a derivative thereof. Thus, where protein function restoration is required, the host cells will typically be derived from cancerous or other diseased cells and naturally produce the disfunctional target protein. Suitable cell lines are available, for example in cell culture collections such as the ATCC and may be derived from osteosarcoma, adenocarcinoma etc., or indeed any established cell line that expresses the mutant protein. Cell lines that lack any expression of the protein of interest can also be used after introducing and expressing the gene encoding the mutated protein. Similarly, cells from other organisms that lack the corresponding gene that can complement the function of such a cell can also be used after introducing and expressing the gene encoding the mutated protein. When the ability of members of a library to modify protein function is under investigation, host cells will typically be chosen which naturally express the target protein under normal growing conditions.

Methods for introducing the library of molecules into host cells are well known in the art. In the preferred embodiments wherein the library is introduced in the form of nucleic acid molecules encoding peptides of interest, standard transfection techniques may be used. Where the library to be introduced comprises peptides or organic molecules, the members of the library may suitably be introduced into host cells by adding members of the compound library to the culture media eg. in the individual wells of a microtitre plate or through the use of microtites, plates or chips on which members of the chemical library are arrayed.

The appropriate reporter system for a given screening method will depend upon the nature of the target protein under investigation. The reporter system is chosen to be responsive to the target protein and thus be capable of indicating the functional status of the target protein. Therefore the reporter system is compatible with or more particularly includes the target protein. The report system preferably comprises a reporter gene which is operably linked to a sequence of nucleotides (e.g. a promoter region) which provides a binding site for the target protein or for a protein which associates with or is a substrate for said target protein.

The mammalian p53 protein illustrates the principle behind a suitable reporter system. P53 functions in mammalian cells mainly through the ability to act as a transcription factor and is a transcriptional activator of several genes associated with cell cycle regulation such as p21, Bax, CD95(Fas/Apo-1) and 4-3-3σ (HME1). It can also down regulate the transcription of cell-cycle-regulating genes such as Bcl2, Cdc2 and cyclin. P53 acts as a checkpoint, monitoring DNA damage and regulating cell cycle progression. Loss of p53 activity predisposes cells to the acquisition of oncogenic mutations and may favour genetic instability—90% of mutations reported in the p53 mutation database are found in the DNA binding domain. Mutations in p53 can lead to cancer formation where p53-mediated apoptosis is deficient due to the mutation.

P21 is one of the p53-transactivated genes that are critical in cell cycle control and many p53 mutants found in cancer cells lose the ability to transactivate p21 transcription. Thus the transactivation level of p21 promoter in a cell reflects whether the p53 protein expressed in that cell has wild type function. As discussed in more detail in the Examples, a p53 reporter system was constructed by cloning human p21 promoter upstream of the puromycin resistance gene. The reporter construct can provide human cells with puromycin resistance only in the presence of wild type or wild-type functioning p53 that transactivates the p21 promoter. Such a reporter system offers significant practical benefits as a lifedeath selection system is possible where only cells with wildtype-functioning p53 can survive when grown in the presence of puromycin.

Thus, while the host cells may have a reporter system as part of their normal genome which can be utilised, typically the host cells will have been modified to include a suitable gene based reporter system. The genetic constructs which comprise all or part of the reporter system will thus have been introduced into the host cells, e.g. by standard transformation/transfection (these terms are used interchangeably herein) techniques, before the screening method is performed. In certain circumstances, the reporter constructs could be introduced at the same time as the molecular library or even, but not preferably, after introduction of the library. Thus for performance of the screening methods of the invention, host cells will preferably have been co-transfected (although not necessarily simultaneously) with a reporter construct and a construct which encodes a peptide. Alternatively members of a chemical compound library, whose ability to restore or modify the function of a target protein is to be investigated, are contacted with the host cells and typically these host cells have been transfected with reporter constructs.

As described in the following Example relating to restoration of function of a mutant form of the *E. coli* tryptophan repressor, two reporter systems, i.e. two different reporter constructs may be used e.g. with one acting as a positive selection survival system and one to confirm restoration potential of the screened peptides.

Target proteins are preferably DNA binding proteins which up or down regulate the expression of other genes through binding to promoter or enhancer regions. Their native gene targets may be utilised to report on whether a target protein function has been restored or modified, but preferably their target DNA binding regions will be operably linked to reporter genes such as genes conferring antibiotic resistance, which encode fluorescent proteins such as GFP (green fluorescent protein), or the much used bacterial reporter enzymes β-galactosidase (-βGal) or β-glucuronidase (β-Gus) etc. According to a particularly convenient and preferred method the protein products of these reporter genes (e.g. β-Gal or β-Gus) could be fused to a signal peptide in order to 'display' the proteins on the cell surface. In this way, the cells expressing the reporter protein can readily be separated physically from other cells that do not express the reporter protein, e.g. by the use of antibodies. Suitable signal peptides are described in the literature and include the signals from a protein such as PDGFR (platelet-derived growth factor receptor). A typical construct would thus be as follows:

Secretion signal peptide—reporter protein (eg. β-Gal/β-Gus)—transmembrane domain, e.g.

```
                                         (SEQ ID NO.: 1)
METDTLLLWVLLLWVPGSTGD
-β-Gal/β-Gus- (SEQ ID. NO.: 2)
AVGQDTQEVIVVPHSLPFKVVVISAILALVVLTIISLIILIMLWQKKP
R-stop.
```

Non-DNA binding proteins can also be used as target proteins provided their wild type activities can be monitored and assayed for or the reporter system engineered such that cell survival depends on restoration of the protein function.

Identification of cells in which the function of the target protein has been restored or modified (e.g. wild-type function has been restored) will depend on the reporter system used. As described above, this is particularly conveniently performed when cells in which wild-type function has not been restored do not survive in the selected culturing environment. Fluorescence detection can also be used to identify cells in which the function of the target protein has been restored or modified. The target protein may, for example, be an enzyme rather than a nucleic acid binding protein and the ability of the target enzyme to act on a substrate may be used as the intracellular reporter system allowing identification of cells in which the function of the target protein has been restored or modified. Other suitable reporter system such as the β-gal. blue/white system are well known in the art and can be used or adapted by the skilled man in his chosen screening method.

In a further aspect, the present invention relates to molecules identified by the screening methods described herein or to derivatives of these molecules. Methods of treatment utilising such molecules and their use in therapy constitute still further aspects of the invention.

Through application of a screening method as described hereby it has surprisingly been found that small molecules e.g. peptides of less than 10 amino acids in length are capable of restoring wild-type function of p53 protein. It is thought that at least 60% of cancers are due to a mutation in p53 which affects function. Ligands identified by the screening methods of the invention have been shown to restore p53 function and cause death of cancer cells.

Thus, in a further aspect, the present invention provides peptides of 2 to 10 amino acids in length, or derivatives thereof, which restore wild-type function of human p53 for use in therapy. Alternatively viewed, the present invention provides peptides of 2 to 10 amino acids in length, or derivatives thereof for use in restoring restore wild-type function of human p53.

The present invention also provides the use of peptides of 2 to 10 amino acids in length, or derivatives thereof, which restore wild-type function of human p53 in the manufacture of a medicament for treating cancer.

Similarly, the invention provides a method of treating cancer in a patient which method comprises administration of one or more peptides of 2 to 10 amino acids in length, or derivatives thereof, which restore wild-type function of human p53.

The identification of such peptides is conveniently achieved by the screening methods described herein and the Examples also describe how the ability of these peptides to restore protein function can be verified.

Peptide "derivatives" as referred to herein include peptides which incorporate side chain modification(s) e.g. modifications of the N-terminal amino group (e.g. by acetylation), the carboxy-terminal group (e.g. by amidation or reduction) or one or more amino acid side chains (e.g. by phosphorylation, acetylation, hydroxylation etc.). Modifications will typically limit degradation of the peptide in vivo and D-amino acids may also be incorporated to reduce degradation. "Derivatives" also include pharmaceutically acceptable salts which have the ability to restore the function of p53 and do not produce any undesirable toxic effects. Examples of suitable salts are the addition salts of inorganic or organic acids such as hydrochloric, phosphoric or acetic acid.

The methods of the present invention are useful for identifying a candidate molecule which can be used as the starting point for development and optimisation work to identify a potential therapeutic molecule. According to the normal techniques of drug development, site directed mutagenesis or site saturation mutagenesis may be used to modify a promising molecule identified by the screening methods of the present invention. Thus in a further embodiment, the present invention provides the use of a molecule identified by a screening method as described herein in a design process to manufacture a therapeutic compound (i.e. a pharmaceutical). Such a design process may involve targeted and random modifications of the stating molecule, the generation of degradation resistant variants thereof or non-peptide mimetics thereof as well as in vivo or in vitro methods of testing these molecules. The invention also relates in an alternative aspect to the use in therapy (e.g. in restoring the function of a target mutant protein) of the molecules resulting from this design process.

The Examples describe suitable methods for determining whether a given peptide or peptide derivative can restore p53 function. As described hereinbefore a useful improvement in p53 function may be achieved without a return to 100% of wild type activity and references to peptides "which restore wild-type function" must be interpreted with that in mind.

Preferably the peptides are 3 to 7 amino acids in length, e.g. 3 to 5 or 6 amino acids in length. Particularly preferred peptides are described herein and include pentamers whose first amino acid is Met and whose second amino acid is Gly Met or Val, the remaining 3 amino acids are preferably, Trp (W), Cys(C) and Thr(T) (in that order). The standard three and one letter amino acid codes are used in this text. Further particularly preferred peptides will be based on the peptides identified according to the screening method described herein but lacking the first Met and second Met, Gly or Val residues as these are required for (stable) expression from a mini-gene but may not be necessary (or even desirable) when the peptide or derivative of it is administered. Thus in a further preferred embodiment the present invention provides peptides or peptide derivatives having 3 to 7 amino acids including the sequence W C T, for use in the treatment of cancer. In order to keep the molecules as small as possible, the peptide or mimetic thereof will preferably have no more than 4 amino acids.

'Peptide derivatives' are discussed above and also include peptides which have a folate group at the N or C terminus, when adding folate to the C terminus a linker group such as lysine or an amide group is used to perform the addition. Further modifications include the N or C terminal addition of the HIV Tat sequence tag. The Tat tag helps translocate the peptide into other organs and thus can be effective against cancer cells which have spread around the body. The Tat tag is a 9-11 amino acid sequence. Folate on the other hand targets cancer cells specifically, as many over-express a folic acid receptor. Thus 'peptide derivatives' include peptides having signal and targeting moieties (which may themselves be peptides) which are typically cleavable to release the active peptide for PFR.

Particularly preferred peptide derivatives include:

```
folate-MGWCT
                              (SEQ ID NO.: 52)
MGWCT-K-folate

Acetyl-MGWCT-amide-folate

Acetyl-WCT-amide-folate

Acetyl-MGWCT-amine-Tat

Folate-WCT

Folate-WCT-amide
                              (SEQ ID NO.: 53)
Acetyl-WCT-K-folate.

(MGWCT is SEQ ID NO.: 3)
```

These small peptides and peptides derivatives are therapeutically convenient active agents and can be readily formulated for administration and delivery.

The peptides, in the form of pharmaceutical compositions, may be administered orally or parenterally by the subcutaneous, intramuscular or intravenous route. Due to their small size, the peptides may be administered by nasal inhalation. The compositions comprise one or more peptides together with a pharmaceutically acceptable carrier therefor and optionally, other therapeutic ingredients. The total amount of active ingredients in the compositions varies from 99.99 to 0.01 percent of weight. The carrier must be acceptable in the sense that it is compatible with other components of the composition and is not deleterious to the recipient thereof.

The compositions may be formulated according to techniques and procedures well known in the art and widely described in the literature, and may comprise any of the known carriers diluents or excipients. Thus, for example, compositions of this invention suitable for parenteral administration conveniently comprise sterile aqueous solutions and/or suspensions of the pharmaceutically active ingredients preferably made isotonic with the blood of the recipient, generally using sodium chloride, glycerin, glucose, mannitol, sorbitol, and the like. In addition, the compositions may contain any of a number of adjuvants such as buffers, preservatives, dispersing agents, agents that promote rapid onset of action or prolonged duration of action and the like.

In addition, the present invention relates to non-peptide compounds showing the same restorative effect on p53 function as displayed by their peptide counterparts. Such peptidomimetics capable of mimicking the activity of the naturally occurring peptide are likely to be better suited for e.g. oral delivery due to their increased chemical stability.

It is now commonplace in the art to replace peptide or protein-based active agents e.g. therapeutic peptides with such peptidomimetics having functionally-equivalent activity. Various molecule libraries and combinatorial chemistry techniques exist and are available to facilitate the identification, selection and/or synthesis of such compounds using standard techniques. The screening methods of the present invention can of course be used to identify suitable peptidomimetics which have the desired restorative effect on p53 function, or a peptide may be identified by the screening method and a peptidomimetic equivalent generated. The Examples herein contain methods which can be used to verify the activity of a candidate molecule in restoring protein function.

A further discussion relevant to the context and appreciation of the present invention is found in our co-pending International application filed 23 Jan. 2003 and claiming first priority from GB 0201523.8.

The invention will now be described in more detail in the following non-limiting Examples which show, inter alia, how molecules may be screened for their ability to affect the function of a target protein in vivo, with reference to the figures in which:

FIG. 1 provides a schematic representation of the construction of p53 reporter p21ur that works in mammalian cells. The p53 transactivated p21 promoter was cloned upstream of puromycin resistant gene, which provided the puromycin resistance to mammalian cells once it was transfected into the mammalian cells which express wild-type functioning p53.

FIG. 2 provides a schematic representation of the generated peptide library plasmid. Each peptide in the library is composed of three random amino acids after two N-terminal amino acids Methioline (Met, or M) and Glycin (Gly, or G). The next three 'X' stands for any amino acid that forms a library consisting of randomly distributed three-amino-acid peptides. The peptide-coding DNA-fragment was inserted into the mammalian expression vector pCEP4 between its KpnI and HindIII site under the CMV promoter. The plasmid has OriP that enables the replication of the plasmid inside mammalian cells. Selection marker expression cassette in the plasmid provides the plasmid-transfected cells with hygromycin resistance.

FIG. 3 gives the results of DNA sequencing of the selected ligand (b) and the empty vector pCEP4 (a), both showed the region between KpnI and HindIII. Both were sequenced by EBV Reverse primer, thus resolved in anti-sense chain. The amino acid sequence of the selected ligand was shown under its encoded anti-sense DNA sequence.

FIG. 4 gives the results, in the form of gel photographs, of RT-PCR analysis of mRNA level of p53 transactivated gene in SW480.7 cells. Results showed that mRNA levels of wild-type p53 transactivated genes p21/WAF1, 14-3-3σ and CD95 were much higher in SW480.7 cells transfected with ligand than that with empty pCEP4. The constitutive expression gene β-actin which was used to normalize total mRNA amount between samples. Arrows point out bands for the target genes. A. RT-PCR for p21/WAF1; B. RT-PCR for 14-3-3σ; C. RT-PCR for CD95; D. RT-PCR for β-actin.

FIG. 5 provides a schematic representation of the construction of pBaxur used in the reporter system described in Example 5.

FIG. 6 provides a schematic representation of the construction of pIRES-EGFP, used in the reporter system described in Example 5.

FIG. 7 provides a schematic representation of the construction of pBaxurEGFP or p21urEGFP, used in the reporter system described in Example 5.

FIG. 8 provides a schematic representation of the construction of pBaxurEGFP-hisD.

FIG. 9 shows in diagramatic form the strategy to screen active ligands that restore the function of cancer causing mutated p53. Here Microgenex (a library of mini-genes encoding peptide ligands) are used but the same strategy can be modified to screen non-peptide ligands.

FIG. 10 is a cartoon giving an overview of the dual selection system of Example 6. In A, the expression the mutant phenyalanyl-tRNA synthase (PheS) permits the incorporation of D,L-p-Cl-Phenyl-Alanine into the growing polypeptide chain resulting in cell death. In B, the restored TrpRT44M mutant binds to the operator promoter fragment and blocks transcription of mutant PheS allowing colonies to form. Likewise, in C the transcription of LacZ is blocked resulting in white colored colonies. Failure of restored TrpRT44M to block LacZ transcription results in blue colonies, seen in D. The pPepLib plasmid is isolated from surviving white colonies and re-transformed into fresh selective conditions to ensure that the TrpR restoration was not transient.

EXAMPLE 1

Figure 1A:
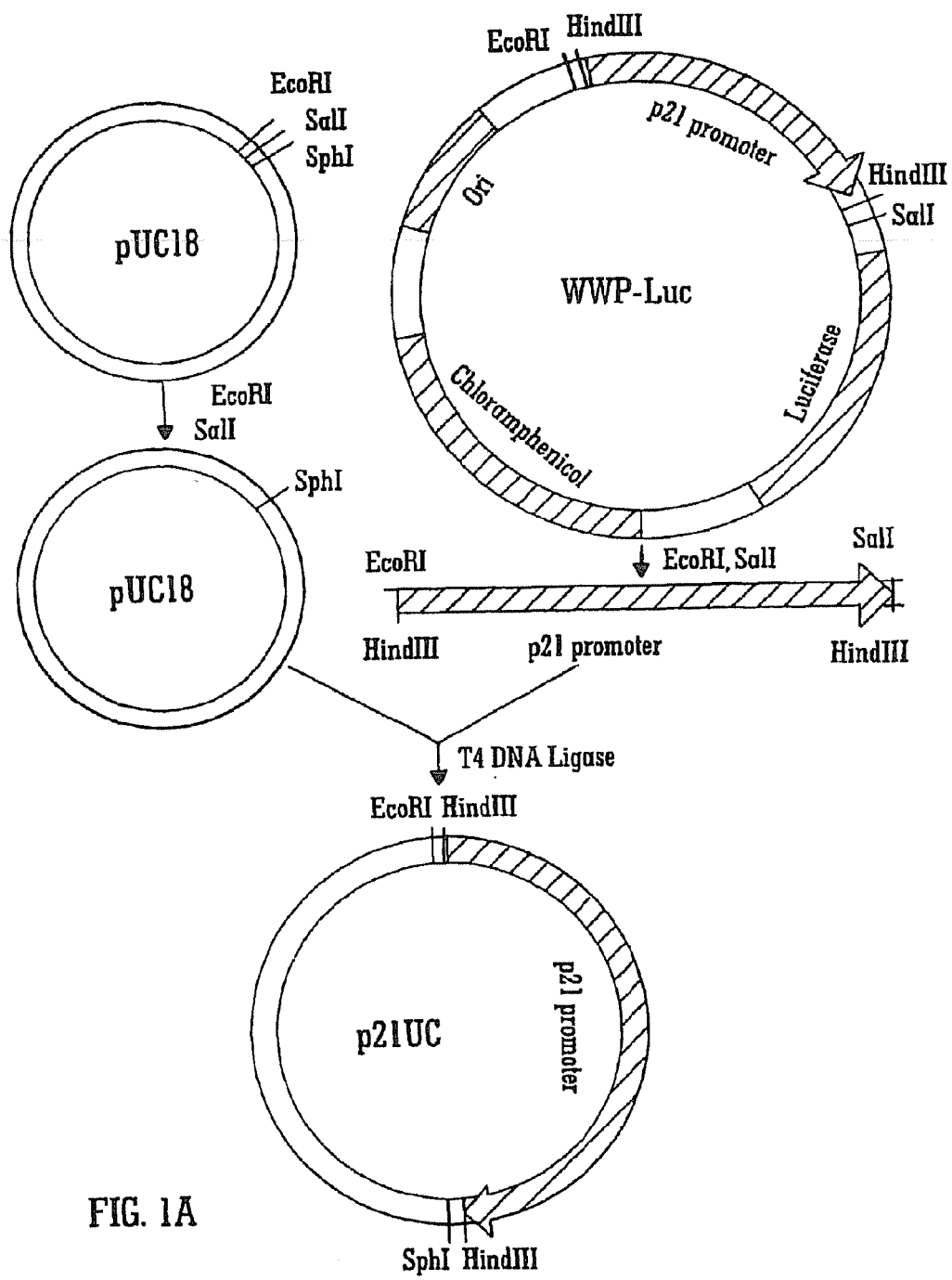

Construction of p53 Reporter Working in Mammalian Cells

The dysfunction of mutant p53 in cancer cells can result from not only the inability in binding to its specific recognized consensus DNA sequence, but also the mal-localization inside cells or incompetent to interact correctly with other transcription co-factors (Vogelstein et al., 2000; Xu & El-Gewely, 2001). The sub-cellular localization mechanism and transcription machinery in mammalian cells is different from that in prokaryotic organisms. The loss of specific DNA binding ability may engage the post-translational modification processes that are totally different from that in prokaryotic organisms. Thus a p53 reporter for mammalian cells has more advantages than that for prokaryotic cells.

P53 protein functions in mammalian cells mainly through its transcriptional factor activity. P21 is one of the p53-transactivated genes that are critical in cell cycle control. P53 can induce cell cycle arrest in G1 phase via transactivation of p21 gene once the cells are under stresses such as DNA damaging. Lots of p53 mutants found in cancer cells lose the ability to transactivate p21 transcription. This leads to not only the vast development of cancer, but also the resistance to cancer chemotherapy and radiotherapy that aim to damage DNA in order to kill cancer cells (El-Diery et al., 1993). Thus the transactivation level of p21 promoter in a cell reflects whether the p53 protein expressed in that cell has wild type function or not.

We constructed our p53 reporter by cloning human p21 promoter upstream of the puromycin resistant gene. It has been reported that basal transcription level from p21 promoter is very low. The reporter can provide human cells puromycin resistance only in the presence of wild type or wild-type-functioning p53 protein that transactivates p21 promoter, while leaving the cells sensitive to puromycin with dysfunctional mutated p53 protein. The advantage to use puromycin resistant gene is to set up a life-death selection: only the cells with wild-type-functioning p53 protein can survive from puromycin selection.

Materials and Methods

Plasmid and vectors used in this Example are WWP-Luc (gift from Prof. Stanbridge E. J.), pPUR (Clontech), and pUC18 (Pharmacia). Enzymes used for cloning are EcoRI (Promega), PvuII (Promega), SalI (Promega), SphI (Promega), T4 DNA ligase (New England BioLab), Klenow (Promega), and SAP (Shrimp Alkaline Phosphotase). Cell lines for the validation of our reporter are U-2 OS cell (ATCC Number: HTB-96, *Homo sapiens* (human), osteosarcoma, bone, wild type p53), Saos-2 cell (ATCC Number: HTB-85, *Homo sapiens* (human), osteosarcoma, bone, p53 null), and SW480.7 (ATCC number: CCL 228, *Homo sapiens* (human), colorectal adenocarcinoma, colon, p53 mutant: R273H/P309S). Medium and other chemicals include McCoy's medium, DME medium, MEM, FCS, calcium phosphate transfection reagents (0.1×TE (pH8.0), 2×HBS (pH7.4), 2M $CaCl_2$, 15% glycerol in HBS), PBS, and puromycin (Sigma).

WWP-Luc plasmid was restricted by EcoRI and SalI. The 2366 bp fragment was gel-purified (1% agarose in 1× TBE) by freeze-thaw method (Wolff & Hull, 1996). Vector pUC18 was restricted by EcoRI and SalI, dephosphorylized by SAP, and purified by phenol-chloroform. Then the p21 promoter fragment was subcloned into pUC18 vector by T4 DNA ligase, generating a plasmid named as p21uc (FIG. 1*a*). All drug resistant markers in the constructed plasimds, are listed in Table 1. Genes involved in the resistance are also listed.

TABLE 1

Drug resistant markers in constructed plasmids and their genes.

| Drug | Resistant gene |
|---|---|
| Puromycin | Puromycin-N-acetyl-transferase (pac) |
| Neomycin | Neomycin phosphotransferase gene |
| Hygromycin B | Hygromycin B phosphotransferase |
| Histidinol | Histidinol dehydrogenase (hisD) |

Figure 1B:
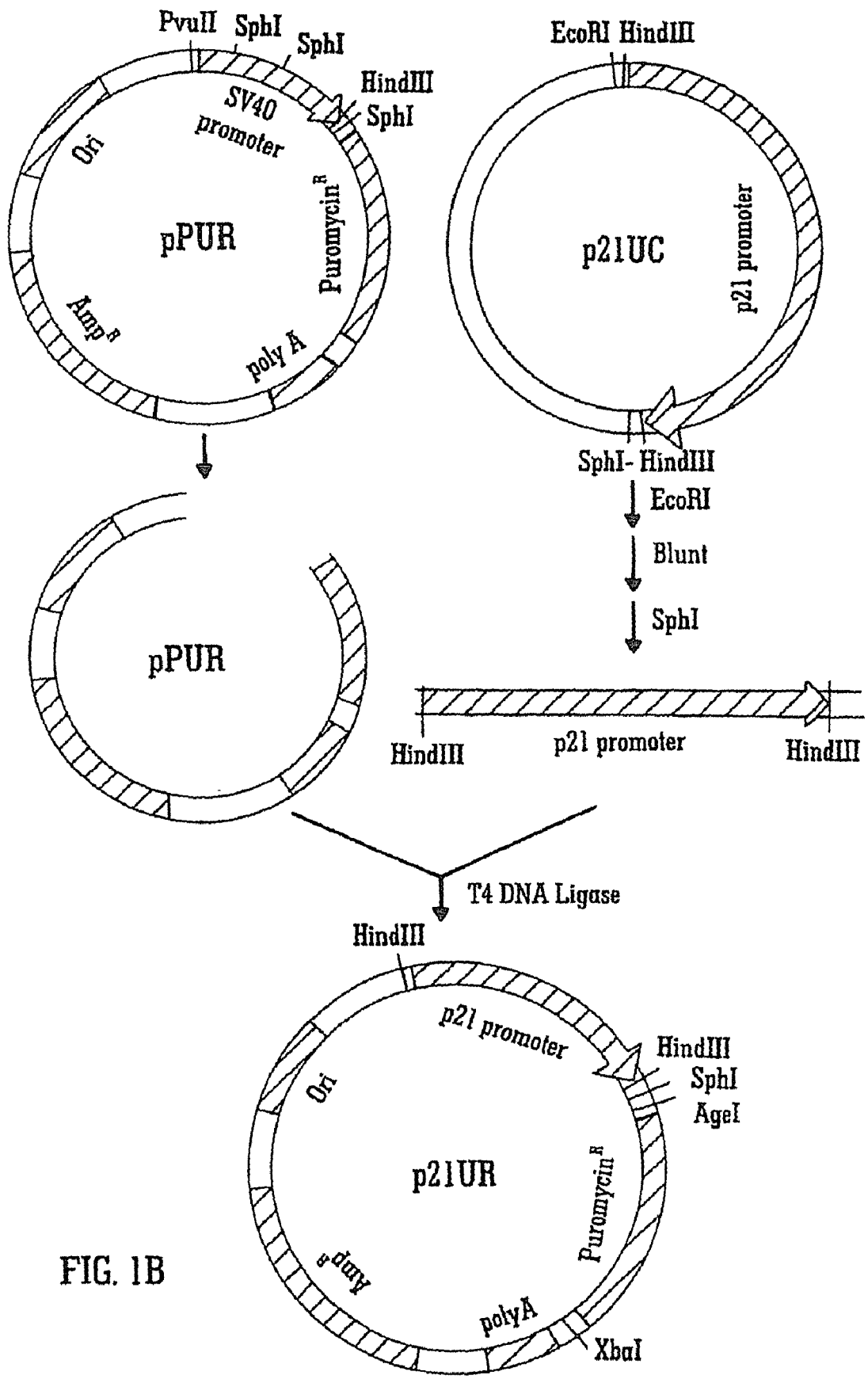

P21 promoter was cut out from p21uc first by EcoRI, blunted with Klenow and dNTP, and then by SphI. The 2450 bp-p21-promoter fragment was gel-purified using the same method as above. Vector pPUR was restricted fully by PvuII and SphI, dephosphorylized by SAP, and gel-purified by the same method, which removed SV40 early promoter upstream of puromycin resistant gene. Finally the p21 promoter was cloned into pPUR vector upstream of puromycin resistant gene by T4 DNA ligase, generating the p53 reporter named as p21ur (FIG. 1*b*).

Verification of the construction was carried out by restriction of the generated plasmid with HindIII. The original vector pPUR has only one HindIII site thus gives one band of 4257 bp after gel electrophoresis. This HindIII site was removed while constructing the reporter p21ur. Two new HindIII sites were introduced into p21ur with the p21 promoter thus can give two bands, one at 2.4 kb and the other at 3.9 kb (FIG. 1).

Validation of the responsiveness of p21ur to p53 was carried out by transfection of p21ur to osteosarcoma cell line U-2 OS that expresses wild type p53 protein, Saos-2 that is p53 null, and colon cell line SW480.7 that expresses R273H and P309S double mutated p53 protein. One day before transfection, 3×10⁵ U-2 OS, 1.5×10⁵ Saos-2, and 3×10⁵ SW480.7 cells were seeded to each well of a 6-well plate. Transfection was carried out by the calcium phosphate method (Parker & Stark, 1979), with 25 µg of p21ur for each well. A 2-minute glycerol-shock was applied 3 hours after DNA was added to the cells and the transfected cells were incubated in MEM/ 10% FCS at 37° C. with 5% $CO_2$ overnight. The transfected cells were transferred to new 6-well plates at the concentration of 5×10⁴ cells per well on the next day, and incubated in growth medium (McCoy's medium/10% FCS for U-2 OS and DME medium/10% FCS for Saos-2 and SW480.7) with puromycin. The same puromycin treatment was also given to the non-transfected cells as a control. Refreshed the medium with puromycin every three-day and observed growth status of the cells.

The cloned vector was restricted by HindIII, which proved that there is the p21 promoter, a ~2.4 kb fragment, inserted upstream of the puromycin resistant gene. DNA electrophoresis showed that the restriction gave two bonds with correct theoretical sizes at 2.4 and 3.9 Kb.

Transfection of the reporter p21ur into U-2 OS cell line provided puromycin resistance to the transfected cells (Table 2). Cells transfected with p21ur kept alive after 5 days of puromycin treatment at 0.5 µg/ml, while the untransfected cells died out. The transfected cells could not survive from higher concentration of puromycin because of the low expression level of p53 protein. Neither transfected Saos-2 cells (null p53) or SW480.7 cells (mutant p53) survived after 5 days of puromycin treatment at the concentration of 0.5n/ml or higher, which proved that the resistance of p21ur-transfected U-2 OS cell to puromycin requires the existence of wild type p53 that transactivates p21 promoter. Thus it validated the proper responsiveness of the reporter p21ur to p53 in human cells.

TABLE 2

Validation of the reporter p21ur - its response to wild type p53 protein.

| Puromycin (µg/ml) | Number of cells attached to the bottom of the well after 5 days of puromycin treatment | |
|---|---|---|
| | Untransfected U-2 OS | Transfected U-2 OS |
| 0 | Growing well | 12600 |
| 0.5 | 0 | 11500 |
| 1 | 0 | <5000 |
| 2 | 0 | <5000 |
| 3 | 0 | <5000 |

EXAMPLE 2

Construction of Peptide Library Expression in Mammalian Cells

We have constructed a microgene library to provide a series of molecular shapes for testing. This 'microgenex' approach enabled us to screen among the expressed peptide repertoire and identify some that could correct mutated p53 and could restore all of its downstream activity.

Selection of the functional peptides can be carried out either in vivo or in vitro according to the peptide library. The advantage of in vivo selection over in vitro selection is that it allows the peptides to carry out their function in an environment similar or even exactly the same as where they will later be applied in therapy. This makes the peptides more applicable and simplifies the modification step for the selected peptides. Besides, it can often detect weak and transient interactions.

Expression of the peptide library allows in vivo screening for possible peptide ligands that can adjust mutant p53 protein back to its wild type function. Once the peptides were constructed into an expression vector, they were easily internalized by cells. With the help of positive-selection reporters, the possible ligands were also readily identified by the recovery of ligand-encoding plasmids from surviving cells. Moreover, according to this technique, there is no need to either synthesize peptides or purify peptides, which can be expensive and labor intensive. An un-integrated, autonomously replicated mammalian expression vector was chosen to prevent the dilution of transfected ligand-encoding plasmids during cell division, or the integration of the plasmids into the host chromosomes, which causes difficulties in rescuing ligand from surviving cells.

Materials and Methods

```
pCEP4 (Invitrogen):
                                    (SEQ. ID. NO.: 4)
TTGACGCAAA TGGGCGGTAG GCGTGTACGG TGGGAGGTCT
         CAAT                                     T
ATATAAGCAG AGCTCGTTTA GTGAACCGTC AGATCTCTAG
ATA         pCEP Forward primer
AAGCTGGGTA CCAGCTGCTA GCAAGCTTGC TAGCGGCCGC
     KpnI                HindIII
TCGAGGCCGG CAAGGCCGGA TCCAGACATG ATAAGATACA TTGATGAGTT TGGACAAACC ACAACTAGAA
  EBV Reverse primer Oligo REGP-10:
                                    (SEQ. ID. NO.: 5)
5'-AAGAGCTCGG TACCAAGAAG GAGTTTACAT ATG GGA NNK
           KpnI                              M   G   X
NNK NNK TGA  TAA GGATCCAAG CTTGAATTCA G-3'
 X   X  stop stop          HindIII Oligo REGP-11:
                                    (SEQ. ID. NO.: 6)
5'-AAGAGCTCGGTACCAAGAAGGAG-3'
          KpnI Oligo REGP-12:
                                    (SEQ. ID. NO.: 7)
5'-CTGAATTCAAGCTTGGATCCTTATC-3'
           HindIII pCEP Forward primer:
                                    (SEQ. ID. NO.: 8)
5'-AGAGCTCGTTTAGTGAACCG-3'

EBV Reverse primer:
                                    (SEQ. ID. No.: 9)
5'-GTGGTTTGTCCAAACTCATC-3'
KpnI, HindIII, T4 DNA ligase, 10xT4 DNA ligase
buffer
```

Oligo REGP-10 was used as a template, while oligos REGP-11 and REGP-12 were used as forward and reverse primers, to generate double-stranded DNA fragments encoding a degenerated peptide library by PCR. The first ATO in this fragment encodes Met as the translation initiation site of the peptides. Gly, the second amino acid encoding by the DNA fragment, assures the peptides expressed are stable inside cells according to the N-end rule (Varshavsky, 1997). The following three repeats of NNK. (N for A, C, G, and T in equal molar ratio, K for G and T in equal molar ratio) code for all possible amino acids and thus form the peptide library. Two stop codens, TGA and TAA, are added right after the last NNK to stop peptide translation. The 5'-end KpnI site and 3'-end HindIII allows the fragments to be cloned into pCEP4 vector in the correct direction under CMV promoter.

After ligation of KpnI/HindIII restricted PCR product and KpnI/HindIII restricted pCEP4, the DNA molecules were electroporated into XL1-blue cells and plated on LB plates with ampicilin. All colonies from the plates were poured together, delivered into small portions and stored at −70° C. Each portion of the transformed cells can be inoculated and start a 1-liter-culture in order to prepared the plasmids by Qiagen Maxi-Prep kit. Insertions were verified by PCR of the generated plasmids with oligos REGPD-11 and REGPD-12. Same PCR reactions were also applied to plasmids prepared from 6 randomly picked colonies so as to estimate the cloning efficiency and the ratio of peptide-encoding plasmids to empty vectors in the population. Note that all generated peptides will start with M and G amino acids followed by three random amino acids.

Results

There were ~25000 colonies on the plates. They were collected into 12 portions. Plasmid prepared from one of such portions was examined by PCR.

Figure 2:
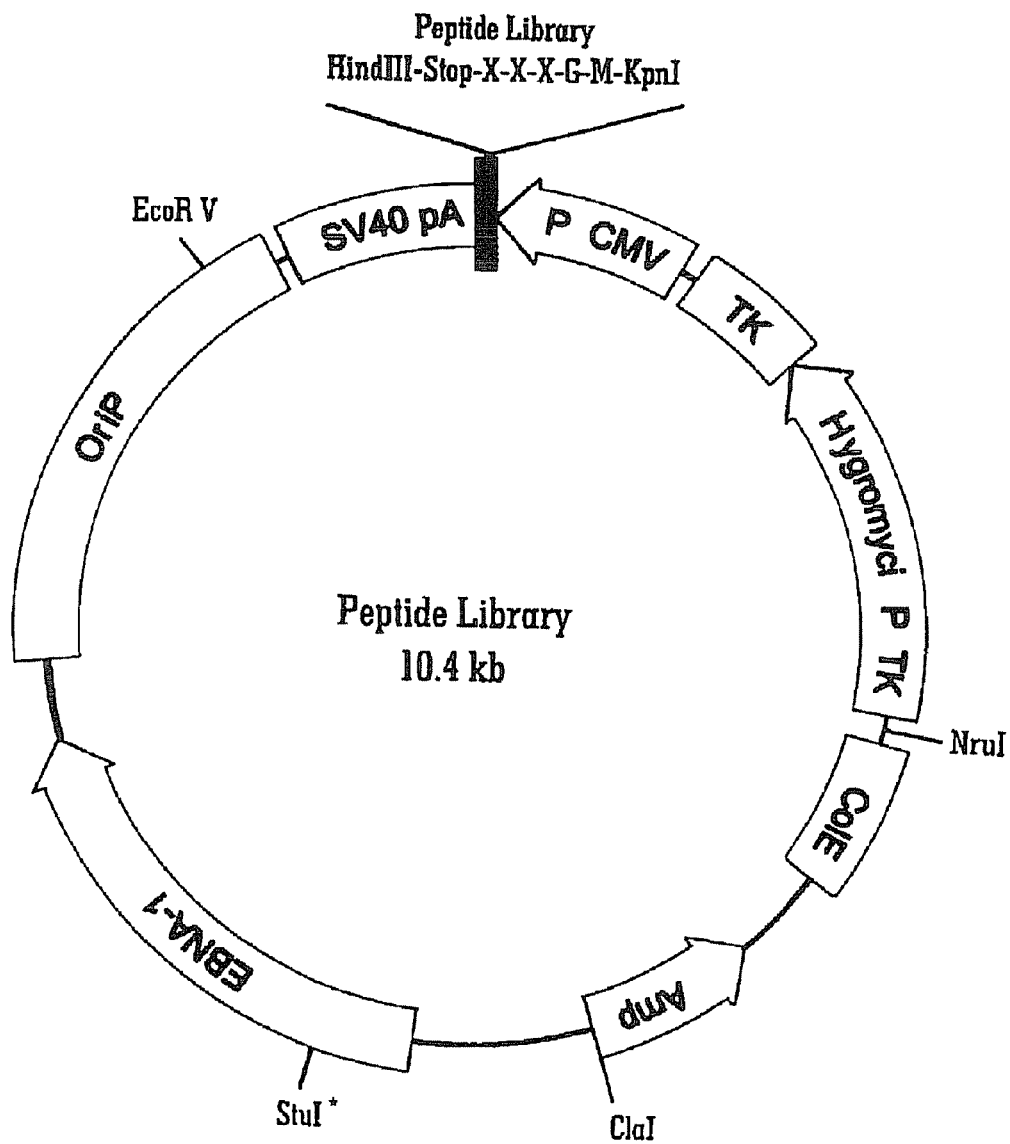
Figure 3:
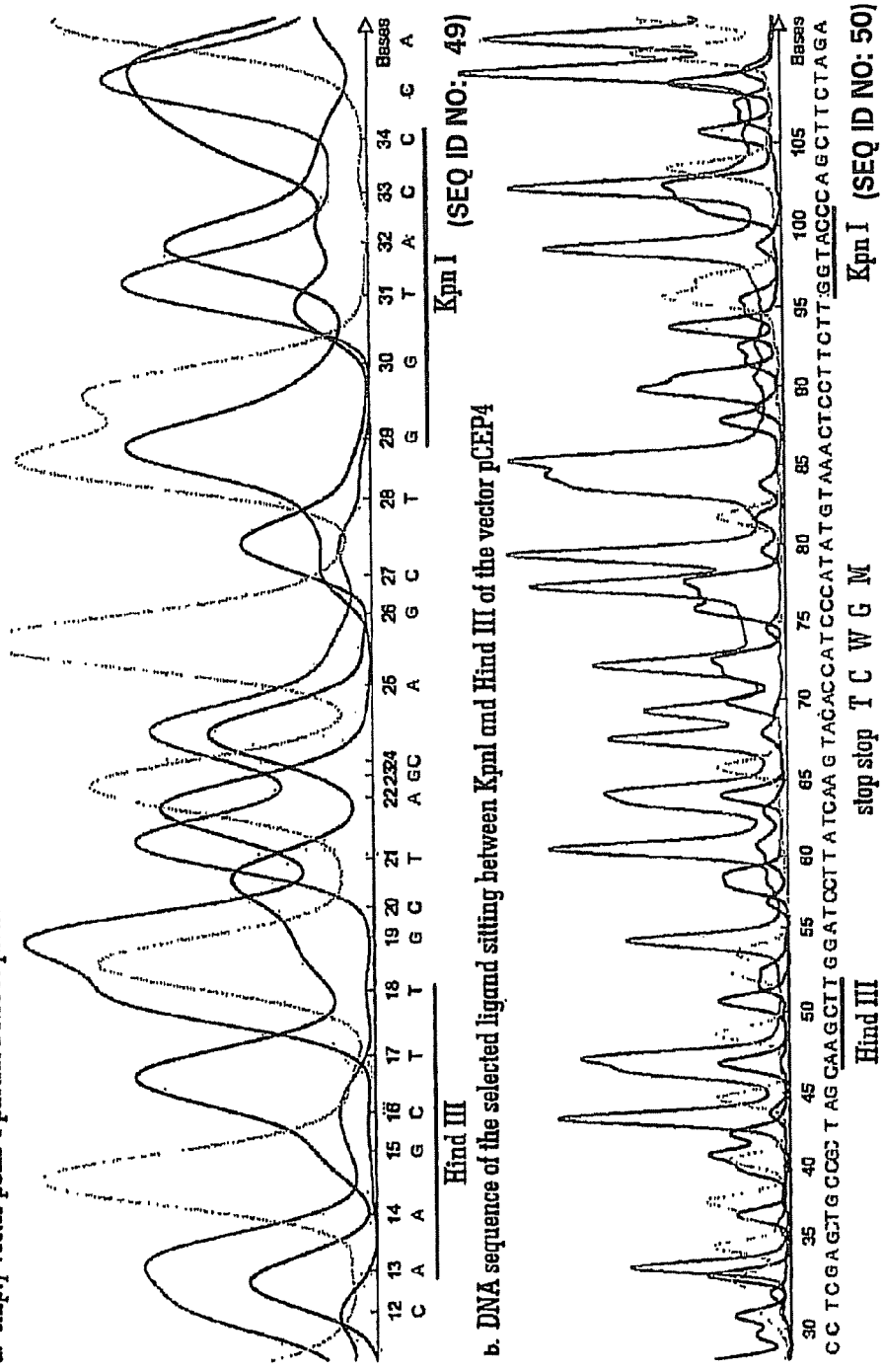

Gel electrophoresis showed that there were insertions with correct size. PCR results from the 6 randomly picked colonies from the original library plates showed that 4 of the colonies had the right construction (showed correct size of insertion) while two did not. The structure of the generated peptide library plasmid is shown in FIG. 2.

EXAMPLE 3

Screening for Ligands That can Correct p53 Mutants in SW480.7 Cells

SW480.7 is a human colon cancer cell line that carries R273H and P309S double mutations in its p53 gene. R273H is one of the most frequently occurred p53 mutations that have been observed in various cancer tissues (Sigal & Rotter, 2000). It has been reported that the p53 mutant in SW480.7 loses its function in transactivating its downstream genes such as p21 (El-Deiry et al., 1993), Bax (Yu et al., 1999), 14-3-3σ. (Hermeking et al., 1997), and CD95 (Fukazawa et al., 1999). Our purpose of screening the peptide library constructed above is to find out one or more peptide ligands that can restore wild-type p53 function without alteration of the mutant p53 gene in the cell and disturbing cells with wild type p53. The choice of a human cancer cell line provides the real human environment in which the selected peptides can be modified, degraded, and transported to subcellular organelles, and thus assures the reliability of the selected peptides to function in human body.

Materials and Methods

Human colon cancer cell line SW480.7 with p53 mutations R273H and P309S (ATCC Number: CCL-228, *Homo sapiens* (human), adenocarcinoma, colorectal; colon), DMEM medium, FCS, PBS, trypsin, puromycin (sigma), hygromycin (sigma), Peptide library (constructed by our laboratory described as above), pCEP4 vector (Invitrogen), calcium phosphate transfection reagents (0.1×TE (pH8.0), 2×HBS (pH7.4), 2M CaCl$_2$, 15% glycerol in HBS).

DNA extraction reagents (TBS buffer (0.8% NaCl, 0.02% KCl, 0.3% Tris, pH7.4), TE buffer (pH8.0), DNA extraction buffer (10 mM TrisCl, 100 mM EDTA, 20 μg/ml RNase, 0.5% SDS, pH8.0), Proteinase K (18 mg/ml), chloroform, phenol (Tris saturated), ethanol, 7.5M ammonium acetate (pH 7.4)), XL1-blue electroporation competent cell, pCEP Forward primer, EBV Reverse primer, dye-terminator thermocyclic DNA sequencing kit, ALF express DNA automatic sequencing system.

The peptide library was transfected into SW480.7 using the calcium phosphate method described in the reporter constructing part. Meanwhile pCEP4 was also transfected into the SW480.7 cells as a negative control. On the second day after transfection, puromycin was added into the medium at the concentration of 0.5 μg/ml. Then the transfected cells were washed with PBS and changed with fresh medium with 0.5 μg/ml puromycin every three days. After all the negative control cells died, all the library-transfected cells that still attached to the wells were collected by scraping into ice-cold TBS buffer.

Rescue of library plasmids was carried out by the extraction of total DNA from the collected puromycin resistant cells according to Blin and Stafford's method (Blin & Stafford, 1976). The extracted DNA was then directly electroporated into the competent cell XL1-blue and plated on LB plates with ampicillin. All the colonies were picked up for plasmid preparation. The plasmids were first screened by size using agarose gel electrophoresis to get rid of the reporters. The rest of the plasmids were sequenced by ALF express DNA automatic sequencing system (Pharmacia) using EBV Reverse sequencing primer (Invitrogen) to reveal the DNA sequence, hence amino acid sequence of the selected peptide ligands.

Results

No pCEP4-transfected cells survived in the well after 7 days of selection with puromycin, while there were still some living library-transfected cells sticking to the bottom of the well.

Electroporation of the DNA extracted from the library-transfected cells after 7 days of selection gave ~150 colonies. Among them, 50 of the colonies have the right size of library plasmid and were sequenced. One ligand peptide sequence was found. The DNA and amino acid sequences are:

```
DNA:
                                           (SEQ. ID. NO.: 10)
5'-GGTACCAAGAAGGAGTTTACATATG GGA TGG TGT ACT TGA
   KpnI
TAA

Amino acid:
M G W C T stop stop

DNA:
                                           (SEQ. ID. NO.: 10)
GGATCCAAGCTT-3'
     HindIII
```

EXAMPLE 4

Validation of the Selected Peptide Ligand

The purpose of this Example is to confirm that the selected peptide ligand indeed restores the mutated p53 protein to the wild-type p53 function in SW480.7 cells. The selection of peptide ligands was based on puromycin resistance. There might be a chance that the cells got the resistance with, or even without the help of the selected ligand via mechanisms other than p53-transactivated p21 promoter. Thus we should make sure that the mutant p53 in SW480.7 cells functions as wild-type p53 only if the selected ligand is added. Confirmation/validation was achieved in two different ways:

1—We observed the function of the peptide ligand on cell cycle control of SW480.7 cells, as well as that of U-2 OS (WTp53) and Saos2 cells (no p53 copy). The selected peptide ligand can be further verified only if it can induce cell cycle arrest or apoptosis in SW480.7 cells but neither in U-2 OS nor in Saos2 cells, which means the specificity of the selected ligand to p53 mutation in SW480.7.

2—We also tested the transcription levels of genes that are only transactivated by wild-type p53. If the transcription levels of these genes are highly induced in ligand treated cells compared with the negative control (cells transfected only with the empty vector (pCEP4). The selected ligand/peptide was proved to be capable of altering the mutant p53 function in SW480.7 into wild-type function.

P53 (wild-type) regulates different cell responses via transactivating different downstream genes. For example p53 causes cell cycle arrest at G1 phase by transactivation of p21 gene. While p53 causes cell arrest at G2 phase by transactivation of CD95 gene. Apoptosis is due to p53 transactivation of 14-3-3 and/or Bax gene (Vogelstein et al., 2000; Xu & El-Gewely, 2001). Thus we measured p21, CD95, and 14-3-3σ gene transcription levels by RT PCR, to reveal the capability of the selected peptide ligand in restoring the wild-type p53 transactivation of the downstream genes. The expression level of β-actin was measured as a control. β-Actin transcription level was used to normalize total mRNA amount between samples for comparison owing to its constitutive expression in all cells.

Materials and Methods

SW480.7, U-2 OS, Saos 2, DMEM, McCoy's medium, FCS, PBS, trypsin, trypan blue (Sigma), calcium phosphate transfection reagents, peptide ligand (selected above), pCEP4 (Invitrogen), TRIZOL® Reagent, chloroform, isopropyl alcohol, 75% ethanol (in DEPC-treated water), 0.01%(v/v) DEPC water, SuperScripII reverse transcriptase (Life Technology), TE buffer (10 mM Tris (pH7.6), 1 mM EDTA), ethanol, 4M ammonium acetate (pH7.0), 1-kb DNA ladder, 10×TBE electrophoresis buffer, 1% agarose in 1×TBE buffer with ethidium bromide.

Primers for RT-PCR are listed in Table 3.

TABLE 3

RT-PCR primer sequences.

| Name | Sequence |
|---|---|
| RT-WAF1-FOR | 5'-CTACCTCAGGCAGCTCAAGC-3' (SEQ. ID. NO.: 11) |
| RT-HME1-FOR | 5'-AGACAGCACCCTCATCATGC-3' (SEQ. ID. NO.: 12) |
| RT-CD95-FOR | 5'-TGGTGCTCATCTTAATGGCC-3' (SEQ. ID. NO.: 13) |
| RT-ACTIN-FOR | 5'-TGACAAAACCTAACTTGCGC-3' (SEQ. ID. NO.: 14) |
| CDS Primer | 5'-AAGCAGTGGTAACAACGCAGAGTACT$_{(30)}$N$_{-1}$-3' (SEQ. ID. NO.: 15) |
| PCR Primer | 5'-AAGCAGTGGTAACAACGCAGAGT-3' (SEQ. ID. NO.: 16) |

Target genes and their corresponding RT-PCR product using the above primers are listed in Table 4.

TABLE 4

RT-PCR primer target genes and their corresponding product.

| Primer name | Target gene Name | Function | Amplify region in target mRNA | Size of RT-PCR product |
|---|---|---|---|---|
| RTWAF1FOR | p21 | G1 arrest | 1514-2121 | 607 bp |
| RTHME1FOR | 14-3-3 | G2 arrest | 652-1245 | 593 bp |
| RTCD95FOR | CD95 | Apoptosis | 1968-2534 | 566 bp |
| RTACTINFOR | β-actin | cytoskeleton | 1236-1793 | 557 bp |

Cells SW480.7, U-2OS, and Sa-os2 were transfected with peptide ligand and pCEP4 parallelly using the calcium phosphate method. The transfection plan was shown in Table 5:

TABLE 5

Transfection plan for the verification of peptide ligand function.

| Cell type | SW480.7 | | U-2OS | | Sa-os2 | |
|---|---|---|---|---|---|---|
| DNA | Ligand | pCEP4 | Ligand | pCEP4 | Ligand | pCEP4 |
| Number of 6-well plates | 3 | 3 | 1 | 1 | 1 | 1 |

After transfection, cells were cultured without drug selection and diluted at the ratio of 1:100 every five days. Cell proliferation status was closely observed until ligand transfected SW480.7 cells died out. Life staining with 0.4% trypan blue was applied to determine the death of the cells. Dead cells can not exclude the dye thus were stained blue. Living cells can pump the dye outside thus were not stained.

Total RNA was collected, from two wells of one ligand transfected SW480.7 plate and one pCEP4 transfected SW480.7 plate each day on day 0, day 1, and day 2 after transfection. Thus RNA samples were harvested as SW480.7/Ligand-0 day, SW480.7/Ligand-1 day, SW480.7/Ligand-2 day, SW480.7/pCEP4-0 day, SW480.7/pCEP4-1 day, SW480.7/pCEP4-2 day. Protocol for total RNA extraction by TRIZOL® Reagent was according to that given by Life Technology:

1. Homogenization

Wash the cell with DEPC water once, then add 1ul of TRIZOL Reagent per well. Pass the cell lysate several times through a pipette.

2. Phase Separation

Incubate the homogenized samples for 5 minutes at room temperature to permit the complete dissociation of nucleoprotein complexes. Add 200 μl of chloroform per 1 ml of TRIZOL Reagent. Cap the sample tubes securely. Shake tubes vigorously by hand for 15 seconds and incubate them at room temperature for 2 to 3 minutes. Centrifuge the samples at no more than 12,000×g for 15 minutes at 2 to 8° C.

3. RNA Precipitation

Transfer the aqueous phase to a fresh tube. Precipitate the RNA by adding 500 μl of isopropyl alcohol per 1 ml of TRIZOL Reagent used for the initial homogenization. Incubate samples at room temperature for 10 minutes and centrifuge at no more than 12,000×g for 10 minutes at 2 to 8° C.

4. RNA Wash

Remove the supernatant. Wash the RNA pellet once with 75% ethanol, adding at least 1 ml of 75% ethanol per 1 ml of TRIZOL Reagent used for the initial homogenization. Mix the sample by vortexing and centrifuge at no more than 7,500×g for 5 minutes at 2 to 8° C.

5. Re-dissolving the RNA

Briefly dry the RNA pellet. Dissolve RNA in DEPC water by passing the solution several times through a pipette tip, and incubation for 10 minutes at 55 to 60° C. Determine the concentration by measure $OD_{260}$. Store at −70° C.

RT-PCR:

First-Strand cDNA Synthesis

1. For each RNA sample, combine the following reagents in a sterile 0.2-ml reaction tube:

| | | |
|---|---|---|
| 1-3 µl | RNA sample | |
| | (using same amount of RNA among samples) | |
| 1 µl | CDS primer (10 µM) | |
| 1 µl | RT forward primer (10 µM) | |
| x µl | Deionized H₂O | |
| 5 µl | Total volume | |

2. Mix and spin the tube briefly.
3. Incubate the tube at 70° C. in a thermal cycler for 2 min.
4. Spin the tube briefly to collect contents at the bottom. Keep tube at room temperature.
5. Add the following to each reaction tube:

| | |
|---|---|
| 2 µl | 5 x First-Strand Buffer |
| 1 µl | DTT (20 mM) |
| 1 µl | 50 x dNTP (10 mM) |
| 1 µl | SuperScripII reverse transcriptase (200 units/µl) |

6. Gently vortex and spin the tubes briefly.
7. Incubate the tubes at 42° C. for 1 hr in an air incubator or cycler.
8. Add 40 µl TE buffer (10 mM Tris (pH7.6), 1 mM EDTA) to dilute the first-strand reaction product.
9. Heat tubes at 72° C. for 7 min to inactivate reverse transcriptase.
10. Samples can be stored at −20° C. for up to three months.

cDNA Amplification by PCR

1. Preheat the PCR thermal cycler to 95° C.
2. For each reaction, 5 µl of diluted first-strand cDNA and 5 µl of deionized water are added to a labeled 0.2-ml reaction tube.
3. Prepare a master mix for all reaction tubes, plus one additional tube. For each reaction:

| | |
|---|---|
| 20.5 µl | Deionized water |
| 5 µl | 10 x PCR buffer |
| 1 µl | 50 x dNTP (10 mM) |
| 1.5 µl | PCR primer (10 µM) |
| 1.5 µl | RT forward primer (10 µM) |
| 10 µl | 5x Q solution |
| 0.5 µl | HotStart Taq DNA polymerase |
| 40 µl | Total volume |

4. Mix by vortexing and spin the tube briefly.
5. Aliquot 40 µl of the PCR Master Mix into each tube from Step 2.
6. Cap the tube, and place it in the preheated thermal cycler.
7. PCR was carried out using the following cycling parameters:

| | | |
|---|---|---|
| | 95° C. | 15 min |
| 2 cycles | 94° C. | 30 sec |
| | 70° C. | 30 sec |
| | 72° C. | 1 min |
| 2 cycles | 94° C. | 30 sec |
| | 69° C. | 30 sec |
| | 72° C. | 1 min |
| 2 cycles | 94° C. | 30 sec |
| | 67° C. | 30 sec |
| | 72° C. | 1 min |
| 2 cycles | 94° C. | 30 sec |
| | 65° C. | 30 sec |
| | 72° C. | 1 min |
| 2 cycles | 94° C. | 30 sec |
| | 63° C. | 30 sec |
| | 72° C. | 1 min |
| 2 cycles | 94° C. | 30 sec |
| | 61° C. | 30 sec |
| | 72° C. | 1 min |
| 2 cycles | 94° C. | 30 sec |
| | 59° C. | 30 sec |
| | 72° C. | 1 min |
| 2 cycles | 94° C. | 30 sec |
| | 57° C. | 30 sec |
| | 72° C. | 1 min |
| 40 cycles | 94° C. | 30 sec |
| | 55° C. | 30 sec |
| | 72° C. | 1 min |
| 1 cycle | 72° C. | 7 min |
| | 4° C. | store |

8. Electrophoreses 5 µl of each PCR reaction alongside 0.1 µg of 1-kb DNA ladder on a 1.2% agarose/EtBr gel in 1× TBE buffer.

Results

After transfecting the ligand into SW480.7 cells for 15 days without puromycin selection, the cells could no longer attach to the wall and died. On the contrary, the ligand-transfected U2-OS and Saos-2 cells were growing well.

Figure 4:
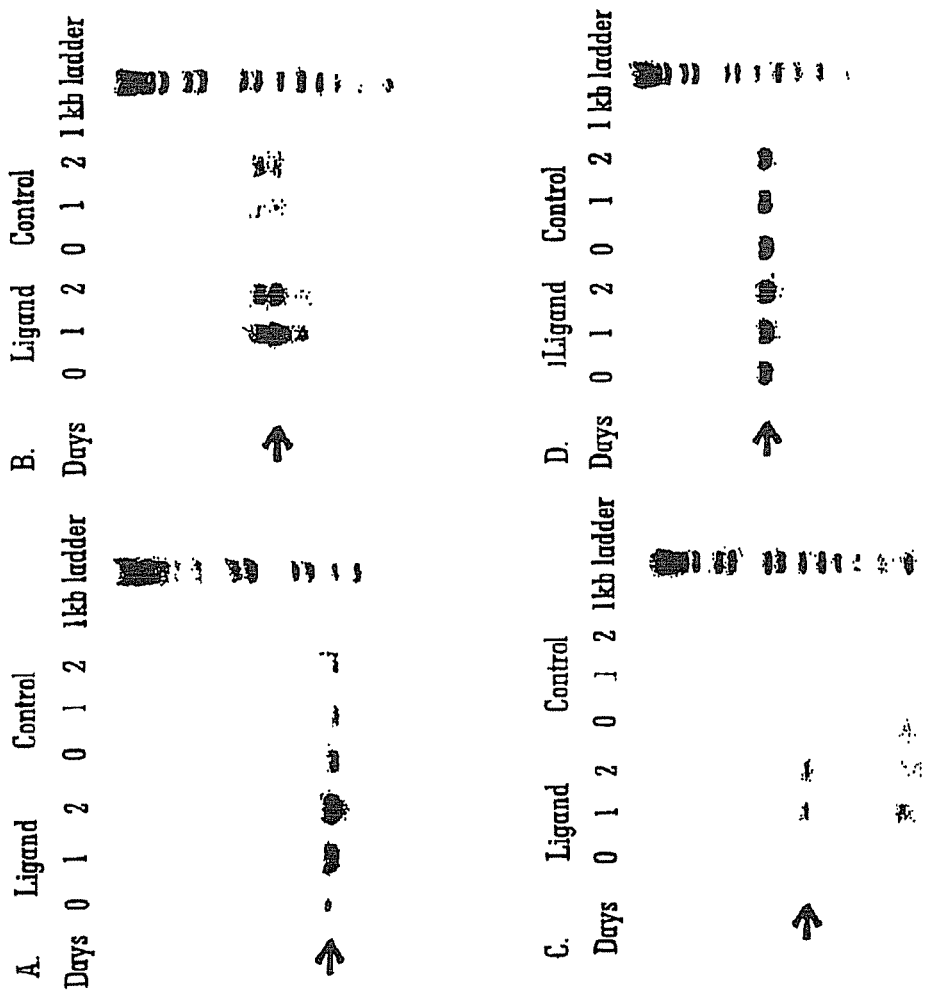

RT-PCR analysis of the mRNA from ligand transfected SW480.7 cells showed that this ligand can reestablish wild type p53 function. Higher mRNA levels of p21 (WAF1/Cip1), 14-3-3σ and CD95 genes were found compared with that in the empty pCEP4 transfected SW480.7 cells (FIG. 4). This proved that the apoptosis and cell growth arrest of ligand transfected cells were owing to the ligand that corrected R273H/P309S p53 mutant to wild type function.

EXAMPLE 5

New Reporter System

The previous p53 reporter p21ur is based on the transactivation activity of wild type p53 to p21 promoter. It has been proved that up-regulation of p21 protein expression will result in cell growth arrest, but not apoptosis. Another p53 target, Bax, can lead to apoptosis once its transcription and expression is upregulated. Bax is one of the key mediators for p53 to induce cell apoptosis—to kill the cells that have failed to repair their damaged genomes (Vogelstein et al., 2000; Xu & El-Gewely, 2001).

Bax promoter is different from p21 promoter, though both have p53 consensus binding sequence. It has been reported that some p53 mutant can transactivate p21 promoter, but not Bax. This indicates a more stringent requirement of p53 conformation for the transactivation of Bax promoter (Thornborrow & Manfredi, 1999).

Green fluorescence protein (GFP) has also been used in the new reporter system. Bax promoter drives a long transcript of both puromycin resistant gene and GFP gene. By inserting an IRES fragment between the two genes that introduces a second ribosome-binding site, they can be translated into protein simultaneously from one transcript (Clontech pIRESneo manual). Thus the green color from GFP will visualize the Bax promoter activity, hence the ligand's activity to correct p53 mutants, in addition to the positive selection of puromycin resistance. The green fluorescence will eliminate the background caused by mechanisms which have cells developed to survive from puromycin selection other than transactivation of Bax promoter.

Selection marker is important for integration of the plasmid into genome. A stable p53-null cell line with integrated reporter system will be convenient for ligand screening, especially for non-peptide ligands.

Materials and Methods

Plasmids used in this Example are: p21ur (above), pIRESneo (Clontech), pEGFP-C1 (Clontech), and pREP8 (Invitrogen).
Genomic DNA (human, male, normal)
Restriction endonucleases (Promega): AgeI, EcoRV, HindIII, NruI, PvuI, SacI, SalI, SpeI, XbaI, XhoI, XmaI.
Modification enzymes: Vent DNA polymerase (NEB), T4 DNA ligase (Promega), and Shrimp alkaline phosphotase (SAP).
Bax promoter primer:

```
Bax promoter Forward:
                              (SEQ. ID. NO.: 17)
5'-atctaagcttgaggcttcagcccgggaattccag-3'
        HindIII Bax promoter Reverse:
                              (SEQ. ID. NO.: 18)
5'-atctaccggtgccagcagtggcgccgtccaacag-3'
        AgeI EGFP primer:
EGFP Forward:
                              (SEQ. ID. NO.: 19)
5'-aataacccgGGTCGCCACCATGGTGAGCAAG-3'
       XmaI EGFP Reverse:
                              (SEQ. ID. NO.: 20)
5'-aataatctagaACTTGTACAGCTCGTCCATGCCG-3'
       XbaI
       stop
```

Figure 5:
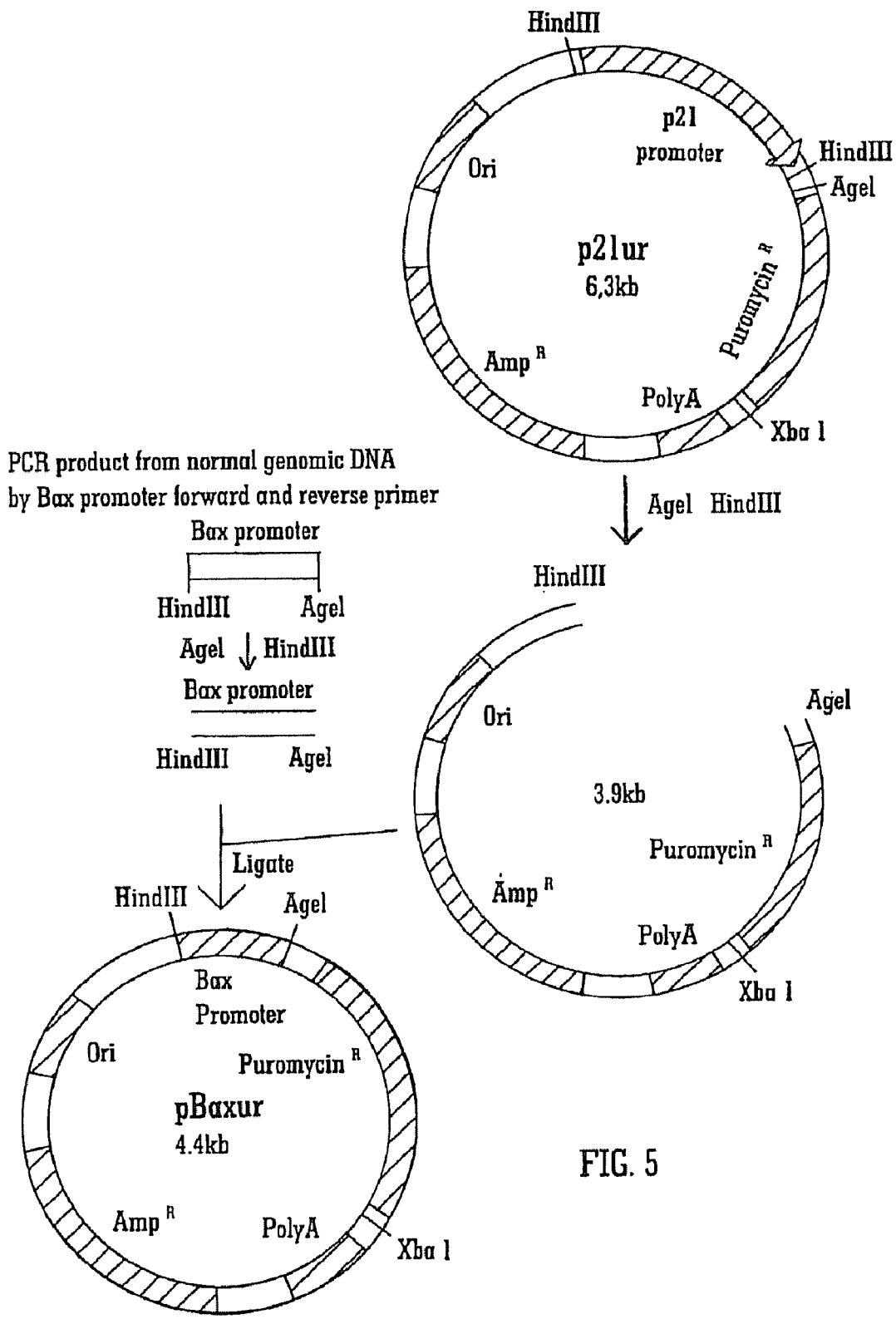

Construction of pBaxur—Bax Promoter Controlled Puromycin Resistant Gene (FIG. 5.):
  Making PCR from normal human genomic DNA using Bax promoter primers.
  The PCR product is 500 bp. It has a SmaI site near its 5'-end and a SacI site near its 3'-end.
  Cut PCR product Bax promoter with HindIII and AgeI.
  Cut p21ur with HindIII and AgeI, and dephosphorylate afterwards. Purify the 3.9 kb fragment from gel.
  Ligate Bax promoter into the 3.9 kb fragment so that Bax promoter can control the puromycin resistant gene expression in mammalian cells. The final product is denoted as pBaxur.

Figure 6:
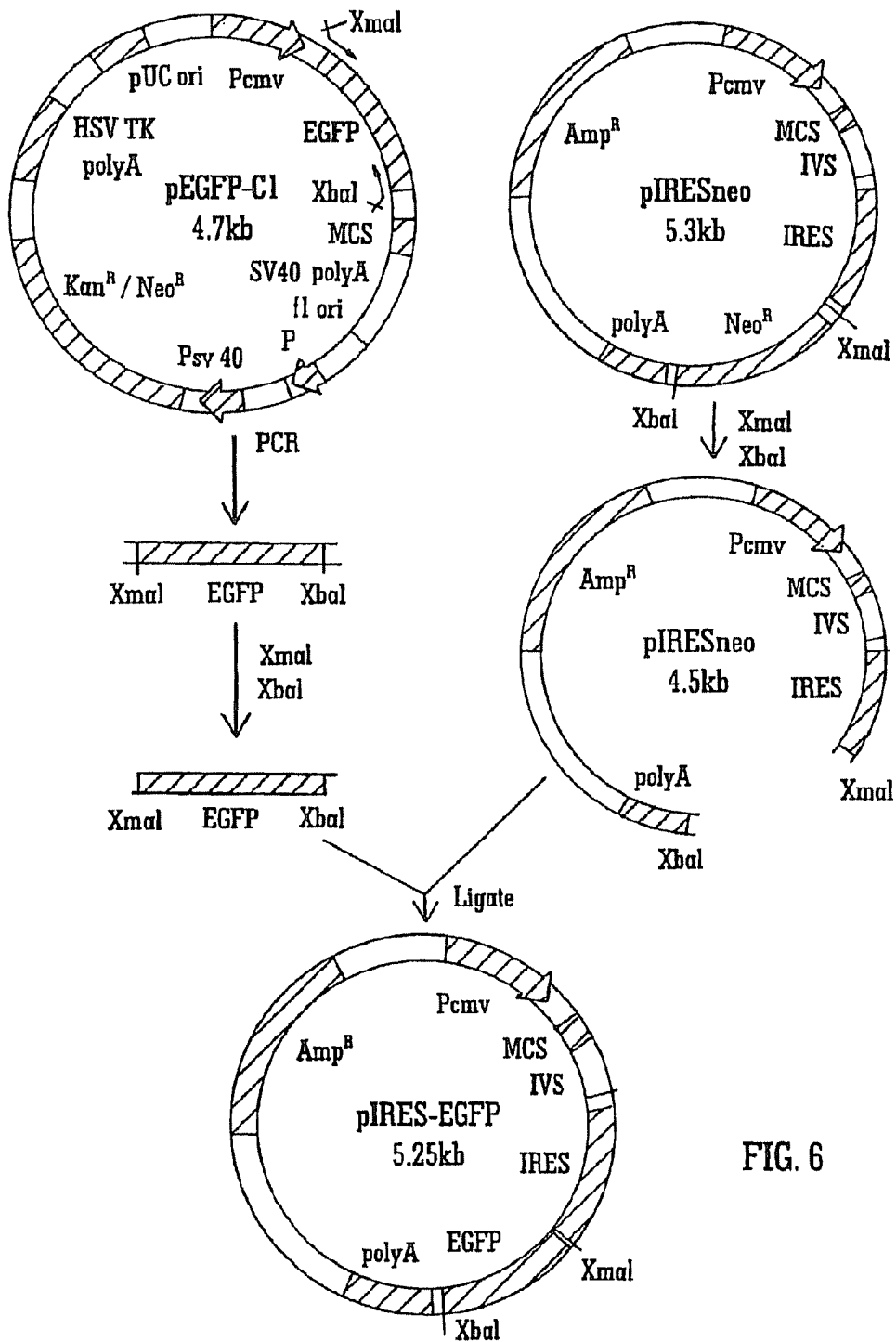
Figure 7:
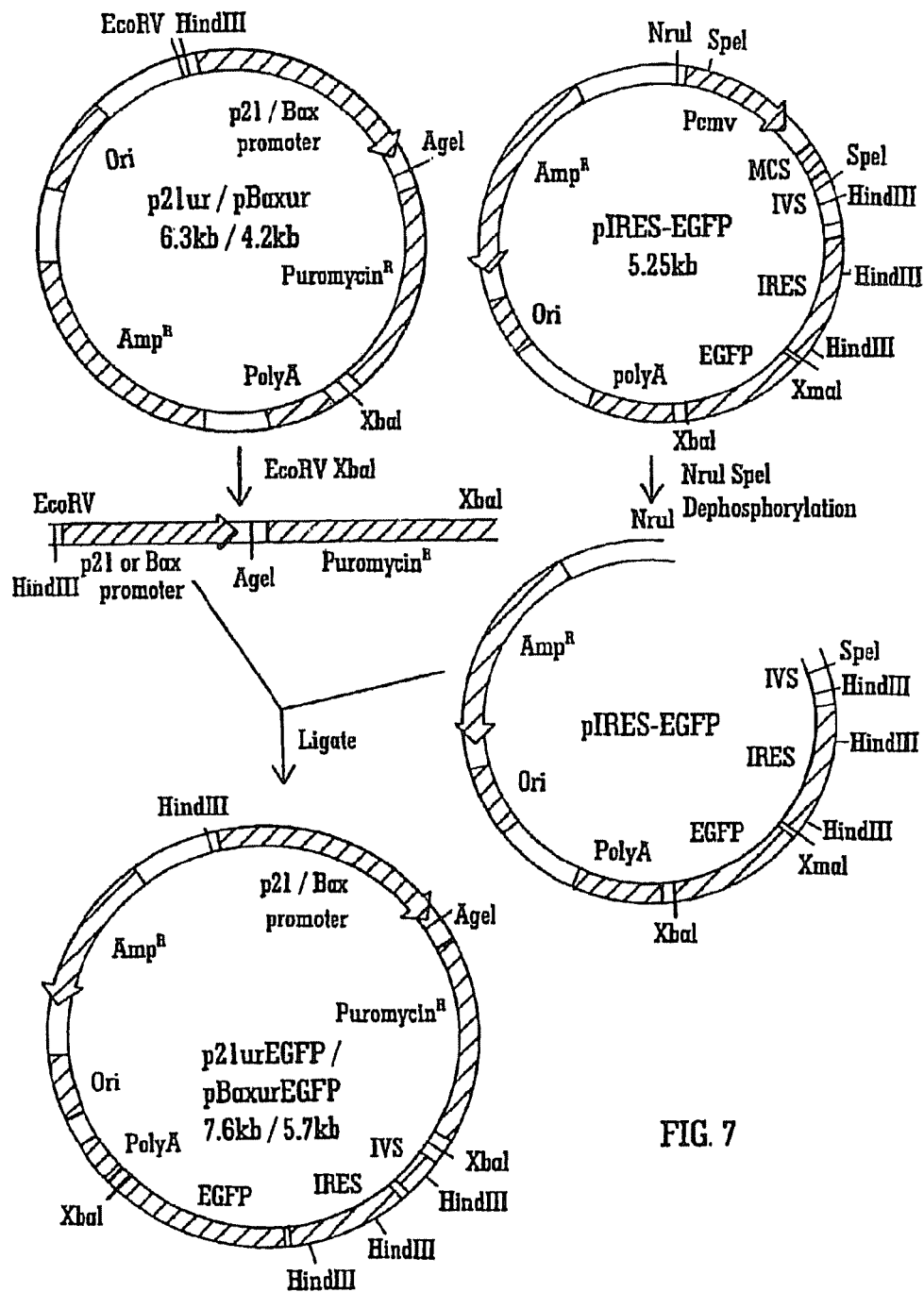

Construction of pBaxurEGFP and p21urEGFP—Green Fluorescent Protein Downstream of Puromycin Resistant Gene that Visualizes the Transcription Level of Bax or p21 Promoter (FIGS. 6, 7):
  Amplify EGFP gene fragment from pEGFP-C1 vector by PCR with the EGFP primers.
  The PCR product is around 750 bp. Cut the product with XmaI and XbaI, then purify it from gel.
  Cut pIRESneo with XmaI and XbaI, then purify the 4.5 kb fragment from gel. Ligate PCR product with pIRESneo 4.5 kb fragment to generate vector pIRES-EGFP (5.2 kb).
  Cut p21ur or pBaxur with EcoRV and XbaI, and purify the 3.2 kb or 1.3 kb fragment from gel.
  Cut pIRES-EGFP with NruI and SpeI, dephosphorylate, and purify the 4.4 kb fragment from gel.
  Ligate the two fragments to generate transient p53-double-reporter p21urEGFP (7.6 kb) or pBaxurEGFP (5.7 kb).

Figure 8:
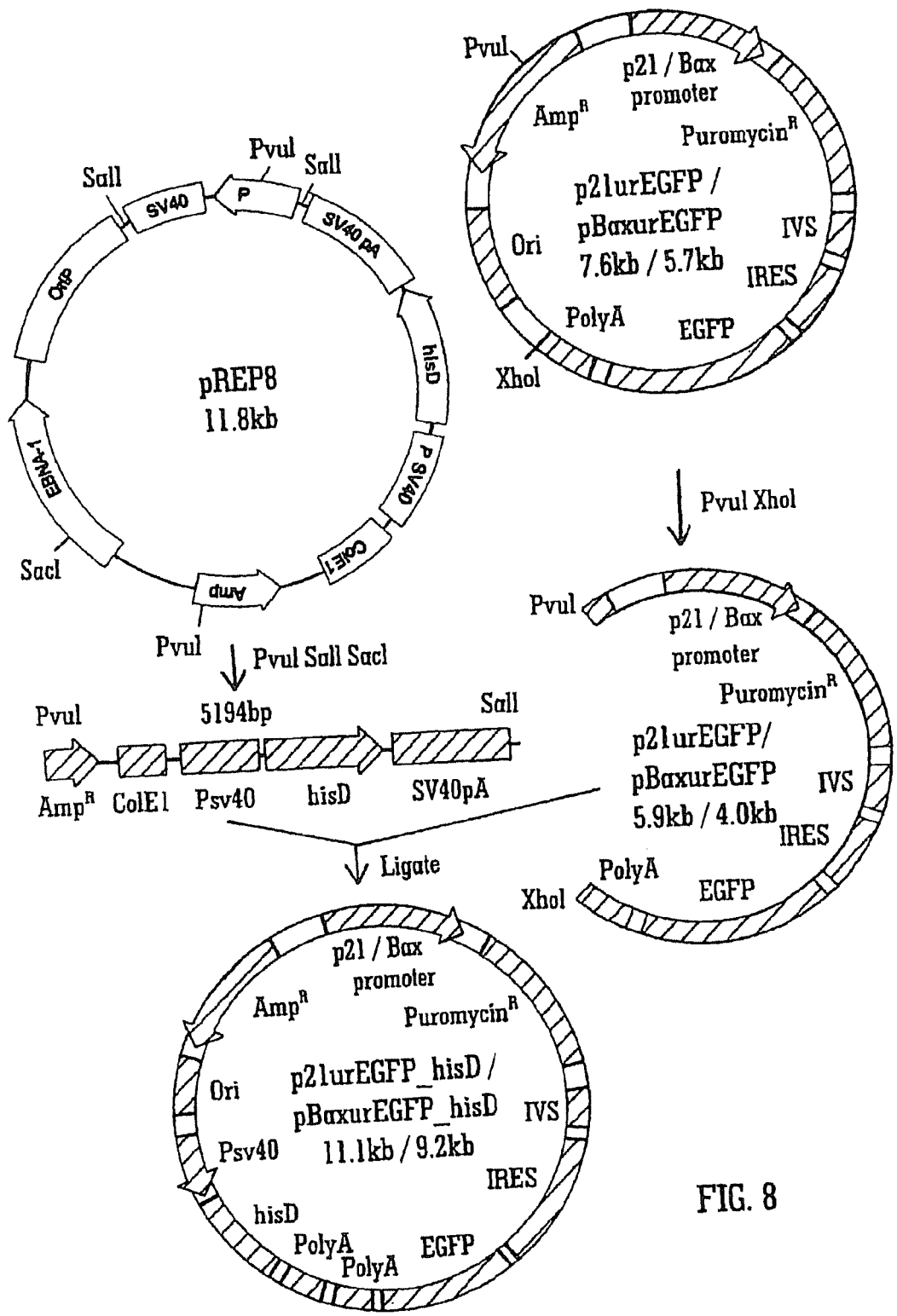
Figure 9:
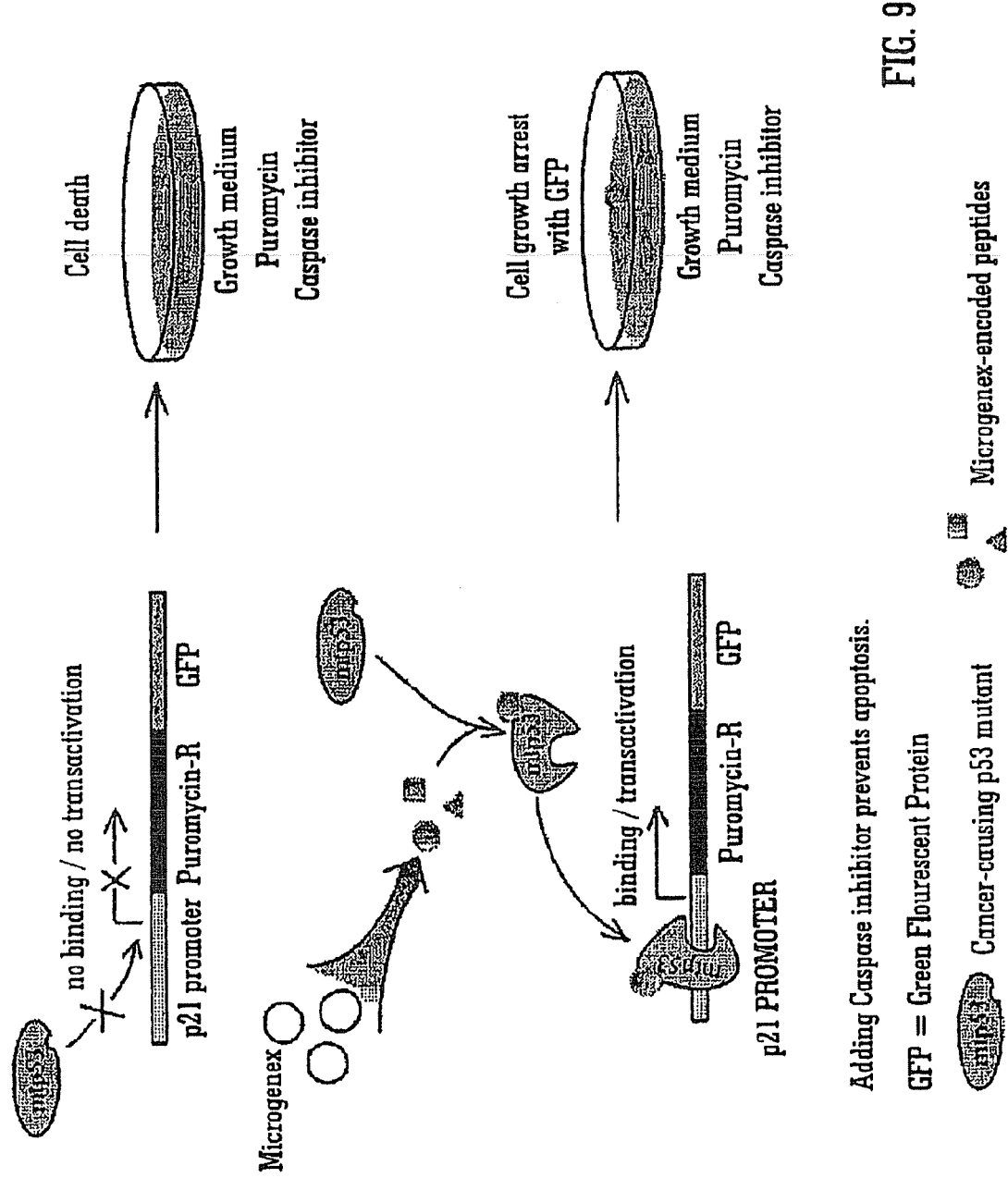

Construction of pBaxurEGFP-hisD—Integrative Plasmid with Selection Mark as Histidinol D Resistant (FIG. 8):
  Cut pREP8 with PvuI, SalI, and SacI, purify the 5194 bp fragment from gel.
  Cut pBaxEGFP with PvuI and XhoI, dephosphorylated, and purify the 3972 bp fragment from gel.
  Ligate the hisD fragment into pBaxurEGFP fragment to generate integrative p53-double reporter pBaxurEGFP_hisD.

The structure of p21urEGFP was verified by restriction of HindIII, which should give five bands of 3489 bp, 2339 bp, 1041 bp, 360 bp, and 348 bp. Agarose gel electrophoresis of the restricted plasmid showed the expected bands.

The structure of pBaxur was verified by restriction of either HindIII together with SacI, which should give two bands of 3996 bp, and 388 bp, or SmaI alone, which should give three bands of 3184 bp, 620 bp, and 580 bp. Agarose gel electrophoresis of the restricted plasmid showed the expected bands.

The structure of pBaxurEGFP was verified by restriction of either EcoRI together with XbaI, which should give two bands of 2907 bp, and 2766 bp, or SacI alone, which should give two bands of 3125 bp, and 2548 bp. Agarose gel electrophoresis of the restricted plasmid showed the expected bands.

The structure of pBaxurEGFP-hisD was verified by restriction of either EcoRI, which should give two bands of 5955 bp, and 3211 bp, or SacI, which should give two bands of 6618 bp, and 2548 bp. Agarose gel electrophoresis of the restricted plasmid showed the expected bands.

Screening for new peptide ligands is done by first transfecting the outlined new reporter p21urEGFP-hisD along with the cotransfection of the peptide library constructed above into cancer cell lines such as SW480.7. Caspase inhibitor VAD-fmk (ApoAlert®, Clontech) is added to the cell culture at the final concentration of 40 mM in order to prevent apoptisis in the case of the overexpression of BAX gene. Also 0.5 µg/ml puromycin is added in the media one-day after transfection. After several days, surviving green cells (excited at 488 nm wavelength) will be the cells containing the cadidate ligands. Rescued plasmids from these cells are subjected to DNA sequencing to deduce the amino acid sequences of the encoded peptide ligands.

When screening non-peptide ligands, a stable cell line of the reporter p21urEGFP-hisD is constructed. Members of the chemical compound library are added to the cell culture. The cells should also be cultured in the medium containing 40 mM VAD-fmk and 0.5 µg/ml puromycin. Surviving green cells after excitation at 488 nm is the indicator for successful candidate ligands.

EXAMPLE 6

Modulation of the *E. coli* Tryptophan Repressor by Expressed Peptides In Vivo

The *E. coli* Tryptophan repressor protein is 107 amino acid, dimeric helix-turn-helix DNA-binding protein. TrpR is a global regulator involved in the transcriptional regulation of 5 unlinked operator regions: tip EDCBA, aroH, trpR, aroL and intr. TrpR regulates both the import of tryptophan (mtr), and the first step in the tryptophan biosynthesis (trpE). Moreover, TrpR regulates two genes within the common aromatic biosynthetic pathway (aroH and aroL), in addition to itself.

In this example we investigate whether a strong negatively complementing TrpR mutant such as T44M could be modulated in vivo by expressed ligands, selected from a pool of expressed ligands. Thereby, restoring the DNA binding function of a non-operative E. coli TrpR(T44M) mutant protein without genetically modifying either the protein, or its cognate DNA target.

In order to select and verify our selected peptide-ligands, a PheS survival reporter system and confirmatory b-galactosidase reporter was used. Several additional experiments were conducted to verify modulation.

Materials and Methods:

TABLE 1

Primers used in Experiment

| | |
|---|---|
| Trp168 Forward: | TCGTAAATCACTGCATAATTCG (SEQ. ID. NO.: 21) |
| Trp168 Reverse: | GTCCATACCCTTTTTACGTGAA (SEQ. ID. NO.: 22) |
| PBad Forward: | GATTAGCGGATCCTACCTGACG (SEQ. ID. NO.: 23) |
| PBad Reverse: | GCCAGGCAAATTCTGTTTTATC (SEQ. ID. NO.: 24) |
| T44M forward: | TCAGGTCGGGAATTATCGCATTAT (SEQ. ID. NO.: 25) |
| T44M Reverse: | TCGCCGTAATGGCTAGTCACATCC (SEQ. ID. NO.: 26) |
| T7 Forward: | TAATACGACTCACTATAGGG (SEQ. ID. NO.: 27) |
| T3 Forward: | ATTAACCCTCACTAAAG (SEQ. ID. NO.: 28) |
| TrpG85E forward: | CGATTACGCGTGAATCTAACAGCC (SEQ. ID. NO.: 29) |
| TrpG85E reverse: | GGCTGTTAGATTCACGCGTAATCG (SEQ. ID. NO.: 30) |
| TrpT44M forward: | CCTGATGCTGATGCCAGATGAGCGC (SEQ. ID. NO.: 31) |
| TrpT44M reverse: | GCGCTCATCTGGCATCAGCATCAGG (SEQ. ID. NO.: 32) |
| PheS forward: | GATAATGTGCGCGTCGAATA (SEQ. ID. NO.: 33) |
| PheS reverse: | TTTGCGGAAACGCAGATCGT (SEQ. ID. NO.: 34) |
| Amp forward: | GTGTCGCCCTTATTCCCTTT (SEQ. ID. NO.: 35) |
| Amp reverse: | GGCACCTCTCTCAGCGATCT (SEQ. ID. NO.: 36) |
| LacZ forward: | AGCGAATACGTCTTCCGTCA (SEQ. ID. NO.: 37) |
| LacZ reverse: | GATGGCTGGTTTCCATCAGT (SEQ. ID. NO.: 38) |

TABLE 2

Media used in Experiment:

YE: (5 g yeast extract, 10 g NaCl, 1 mM tryptophan, Ampicillin 200 ug/ml, add $H_2O$ to 1 litre)
YEA: (YE with 0.2% Arabinose, 0.2% CAA)
YEG: (YE with 0.2% Glucose)
YEPG: (YEG with 2 g DL-p-Cl-phenylalanine [ ®Sigma, St. Louis, Mo. USA])
YEPA: (YEA with 2 g DL-p-Cl-phenylalanine)
LB: (10 g Bacto Tryptone, 5 g Bacto Yeast Extract, 10 g NaCl)
BTTR: (10 g bacto-tryptone, 5 g NaCl, X-gal 40 μg/ml, 1 mM tryptophan, phenylethyl-D-galactopyranoside [ ®Sigma, St. Louis, Mo. USA], $dH_2O$ to 1 L)
BTTRA: (BTTR with 200 g/ml Ampicillin, 2 g/L DL-p-Cl-phenylalanine, 2% Arabinose)
BTTRG: (BTTR with 200 g/ml Ampicillin, 2 g/L DL-p-Cl-phenylalanine, 2% Glucose)
Bactotryptone plates: (BTTRA of BTTRG with 15 g agar/L)

TABLE 3

Solutions used in Experiment:

Sample Buffer I: (0.3% SDS, 200 mM DTT, 50 mM Tris 8.0, protein inhibitor cocktail of choice)
Sample Buffer II: (500 mM Tris ph 8.0, 50 mM MgCl2, 1 mg/ml DNAseI, 0.25 mg/ml RNAse A, or 0.1 mg/ml Benzonaze instead of (DNA/RNAse)).
Rehydration: (8 mol/L Urea 24 g, 0.5% CHAPS 250 mg, 0.25% Pharmalytes 3-10 310 ul, 0.2% DTT 100 mg, 0.01% Bromophenol blue 1 mg, add water to 50 ml)
ESS: (2% SDS 2.0 g, 6 mol/L Urea 36 g, 0.1 mmol/L EDTA, 3 mg, 0.01% Bromophenol Blue 10 mg, 50 mmol/L trisHCl pH 6.8 10 ml, 30% Glycerol (v/v) 35 ml of 87% solution, add 100 ml dH2O)
Sample Application Buffer: (Urea 8M, CHAPS 4% w/v, Tris 40 mm pH 8.0, DTT 65 mm)
Cathode buffer 10x: (Tris 30.4 g, Glycine 144 g, SDS 10 g, in 1 L dH2O)
Anode buffer 10x: (Tris 30.4 g, fill with dH2O to 800 ml, titrate with 4M HCl to pH 8.4, fill to 1 L)
Light 8% solution: (50 ml acrylamide 40%(37.5:1), 145 ml dH2O, 75 ml 4 x slab buffer, 30 ml glycerol, 300 μl TEMED)
Heavy 16% solution: (115 ml acrylamide 40%(37.5:1), 35 ml dH2O, 75 ml 4 x slab buffer, 75 ml glycerol, 300 ul TEMED)
Slab buffer 4x: (Tris 181.8 g, fill with dH2O to 800 ml, titrate with 4M HCl to pH 8.8, fill to 1 L)
SDS lysis solution: 2% SDS, 16 mM EDTA (add 200 mM NaCl if cells are grown in low salt media like LB).

TABLE 4

Cell Lines and Plasmids used in Experiment

λRTLF - W3110, tnaA2, trpR2, Δlac169, [λ, trpOP, trpL'-trpE'-lacZ', lacY, λ] (Paluh, J. L. et al. Nucleic Acids Res. (1986) 14: 7851-60)
XL1-Blue*- recA1, endA1, gyrA96, thi-1, hsdR17, supE44, relA1, lac[F' proAB lacI$^q$ZΔ M15 Tn10 (Tet$^r$)]$^c$
pBAD33- cam$^r$, p15a-origin, AraC, pBAD (Guzman, L. M. et al. J. Bacteriol (1995) 177: 4121-30)
pTrpRep- amp$^r$, pMB1-origin, TrpEDCBA • OP'-pheS, tet • OP'-trpR (current study)
pKSS- amp$^r$, pUC-origin, lacI, lacZop, f1, pheS*(Ala-Gly294) (Kast, P. Gene (1994) 138: 109-114)

*Stratagene, 11011 North Torrey Pines Road, La Jolla, CA 92037

Construction of the pTrpRep(None) Reporter:

E. coli genomic DNA was extracted using standard procedures and used as a template along with the Trp168 primers (Table 1) to initiate the following PCR reaction resulting in a 168 bp fragment. PCR reaction: Trp168 forward and reverse primers 20 mm, template 500 ng, $MgCl_2$ 3 mM, dNTP 0.2 mM, 1 unit Pfu Turbo™ (Stratagene), 5μl 10× reaction buffer, $dH_2O$ to total 50 μl. The 168 bp PCR fragment containing the TrpEDCBA promoter operator was cleaned using the Qia quick PCR cleanup kit. Two microliters of pKSS vector was cut with ClaI restriction enzyme for 90 minutes at 37° C. according to the manufactures instruction. ClaI restriction was in Promega buffer C. Following ClaI restriction, 1 unit of T4 DNA polymerase and 0.2 mM dNTP were added directly to the reaction and the sample and incubated at 37° C. for an additional 10 minutes. The entire 168 bp fragment was then purified from an agarose gel using the Qia quick clean kit. Two hundred nanograms of purified ClaI cut, T4 flush ended, pKSS vector was added to 200 nanogram of the 168 bp TrpEDCBA PCR fragment along with 40 units of T4 DNA ligase and ligase buffer in a total of 8 µl and incubated overnight at 18° C. Two microlitres of the ligation reaction were mixed with XL1 competent cells prepared using Inoue et al 1990, Gene 96, 23-28 and plated out on LB plates with 0.2% glucose and 200 µg/ml ampicillin. Verification of 168 bp DNA fragment and fragment orientation was by speI restriction enzyme digestion. DNA sequence verification was done using the T3 forward primer. The resulting plasmid with the PheS gene under the transcriptional control of the TrpED-CBA operator promoter was called pTrpRep(None)

Construction of the pTrpRep(WT) Reporter:

The constitutive tet promoter and TrpR protein-encoding fragment was cut using enzymes XbaI and SphI from pACYC184-trpWT (Storbakk, N. C. et al. J. Mol. Biol. 256: 889, 896). The 1141 bp fragment was blunted as above and gel-purified. Two microlitres of pKSS vector containing the TrpEDCBA operator fragment was digested with NotI and subjected to the DNA overhangs filled with T4 polymerase using standard methods. The pTrpRep(None) vector was then gel purified as above. Approximately, 200 ng of the pTrpRep (None) vector was mixed with 500 ng of 1141 bp tet-TrpED-CBA operator fragment along with 40 units of T4 DNA ligase and incubated overnight at 18° C. Competent IRTLF cells were transformed with 2 µl of the ligation mix and plated out on LB media with 0.2% glucose and 200 µg/ml ampicillin. Continuation of insert was by blue/white screening on bactotryptone plates (Table 3), by restriction enzyme analysis and by sequencing using T3 and T7 primers (Table 1). The verified vector construct was called pTrpRep(WT).

Construction of pTrpRep(T44M) and pTrpRep(G85E):

The wild type gene encoding for the tryptophan repressor protein was mutated by Stratagene's Quick-change™ site-directed mutagenesis kit to introduce a methionine residue at the 44 threonine position and a glutamate residue at the glycine 85 position. Primers used for mutagenesis are listed in Table 1: G85E forward, G85E reverse, T44M forward, T44M reverse. Sequence verifications were through DNA sequencing using the T7 and T3 primers.

Construction of pPepLib:

A peptide expression library was constructed to express under the arabinose promoter of the pBAD33 plasmid. For details see Example 7 herein.

Reporter System Verification:

Two 50 milliliters cultures of RTLF cells containing either pTrpRep(WT) or pTrpRep(T44M) vector plasmids were grown in LB media at 30 C with shaking to a density of 0.6 at wavelength 600 nm. Cells were diluted 1 to 5000 in the YE media. A 250 µl aliquot of the two diluted cultures were then plated onto YE plates with 0.2% glucose, with or without 1 mM tryptophan (+/−W) and with or without DL-p-Cl-phenylalanine(+/−P) at 2 g per liter. An overview as well as results can be seen in Table 4.

Isolation of the active peptide ligand for pTrpRep(T44M): DNA was isolated from 50 ml cultures of surviving white TrpT44Mrep/pPepLib colonies on YEPA plates using the Quiagen Midiprep Kit™ and protocol. The DNA was then restricted for 90 minutes at 37° C. with restriction enzyme speI which cuts only in the pTrpRep(T44M) vector and hopefully not in pPepLib. Competent XL1 cells were transformed with the restricted DNA and plated out on to LB plates with 25 µpg/ml chloramphenicol. Consequent colonies were then replica-plated onto LB plates with 25 µg/ml chloramphenicol as well as plates with 200 µl/ml ampicillin. Colonies that grew in the presence of chloramphenicol but not ampicillin were assumed to have lost the TrpT44M vector.

Selection of an Active Microgene:

RTLF cells containing the pTrpRep(WT) were transformed with pPepLib and the pBAD33 control vector. Likewise, RTLF cells containing the TrpRep(T44M) reporter constructs were transformed with pPepLib and the pBAD33 control vector. Cells were grown in LB media at 30° C. with shaking to an OD 0.6 at wavelength 600 nm. Cells were diluted 1 to 5000 in the media (YEG or YEA with 25 µg/ml chloramphenicol) and 250 µl plated out on plates (YEG, YEPG, YEA, YEPA, with 25 µg/ml chloramphenicol). All surviving white colonies from the TrpT44Mrep/pPepLib transformation on YEPA plates were harvested and transferred to LB media with 25 µg/ml chloramphenicol for amplification and DNA isolation.

Re-Transformation of the Rescued pPepLib Peptide:

One microliter of the isolated pPepLib (100 ng), and 1 µl of pBAD33 (100 ng), were transformed into a fresh RTLF culture containing the TrpRep(T44M) reporter vector were plated out on to YEPA plates 25 µg/ml chloramphenicol. Plates that showed an abundance of white colonies were assumed to code for a peptide that restored TrpR DNA binding function. The pPeplib plasmid was sequenced using Amershams Alpha express automatic sequencer and Cy5 dye terminator kit. Primers used in the sequencing reaction were pBad forward and pBad reverse primers (Table 1).

β-Galactosidase:

A λRTLF culture containing pTrpRep(WT), pTrpRep(T44M), pTrprG85E, and pTrpRep(None) were transformed with one of pPep(MGFLR) or pPep(MGFWR), and grown in both BTTRG and BTTRA media to an OD of 0.6 at wavelength 600 at 30° C. with shaking. Two hundred microliters of cultures assayed for β-galactosidase levels at wavelength 405 nm as described in Fenton et al (1998) BBRC 242(1):71-78.

λRTLF cultures containing one of pTrpRep(WT), pTrpRep(T44M), pTrprG85E, or pTrpRep(None) were grown in BTTRG media supplemented with one of following synthesized peptides MGFLR, MGFWR, MGRRW, FLR, FWR at a concentration of 1 mM. The cultures were grown to an OD of 0.6 at wavelength 600 at 30° C. with shaking. Two hundred microlitres of cultures assayed for -galactosidase levels at wavelength 405 as described in Fenton et al (1998) supra.

Effect of Tryptophan Corepressor on b-Galactosidase Values with Plasmids:

A λRTLF culture containing pTrpRep(WT), pTrpRep(T44M), pTrprG85E, and pTrpRep(None) were transformed with one of pPep(MGFLR) or pPep(MGFWR), and grown in BTTRA media with and without tryptophan to an OD of 0.6 at wavelength 600 at 30° C. with shaking. Two hundred microliters of cultures assayed for -galactosidase levels at wavelength 405 as described in Fenton et al (1998) supra.

Effect of Tryptophan on β-Galactosidase Values with Plasmids:

λRTLF cultures containing pTrpRep(T44M) were grown in BTTRG media, with and without tryptophan, and supplemented with one of following synthesized peptides MGFLR, MGFWR, MGRRW, FLR, FWR at a concentration of 1 mM. The cultures were grown to an OD of 0.6 at wavelength 600 at 30° C. with shaking. Two hundred microlitres of cultures assayed for b-galactosidase levels at wavelength 405.

Two Dimensional Gel Electrophoresis:

Rehydration:

Eighteen centimeter long Immobiline DryStrips pH 3-11 from Pharamicia were rehydrated overnight in the rehydration solution (Table 2)

E. coli Protein Sample Preparation:

A two hundred milliliters of the λRTLF culture containing plasmids pPep(MGFWR) and TrpRep(T44M) was grown on YEA media with 25 μg/ml chloramphenicol until an OD of 0.6 at wavelength 600 nm. Likewise, two hundred milliliters of the control λRTLF culture containing plasmids pBAD33 and TrpT44Mrep was grown on YEA media with, 25 μg/ml chloramphenicol until an OD of 0.6 at wavelength 600 nm. The two 200 ml cultures were harvested and centrifuged at 5000 rpm for 10 minutes in a SS34 rotor at 4° C. Cells were re-suspended in 2 ml of sample buffer I (Table 3), 40 μl of sample buffer II (Table 2) was added and the cell paste incubated at 37° C. for 60 minutes. The lysate was not overly viscous at this point. Five microliters of the cell paste was added to 175 μl of sample application buffer (Table 3). The samples were spun in a microcentrifuge for 15 minutes at maximum speed before application into the sample applicator cups of the first dimension of the Pharmacia 2Dgel system.

Running the 2D Gel:

The IPG strips were run at 150V, 1 mA, 1 W, for 90 minutes followed by a second step of 3000V, 1 mA, 1 W for 15 hours. The strips were rinsed briefly with $dH_2O$ and equilibrated twice in 5 ml ESS buffer (Table 3). Following equilibration the strips were placed on top of 8-16% gradient slab gels and encased in warm 1× cathode buffer (Table 3) with 0.6% agarose. The gradient gels were cast using a gravity driven gradient mixer with heavy solution (Table 3) in the reservoir chamber and the light solution in the mixing chamber (Table 3). To initiate polymerization at the upper light edge 300 ul 15% APS was added to the light (8%) solution and 220 ul 15% APS to the heavy (16%) solution.

Silver Staining:

Gels were silver stained as follows.

1×30 minutes in 50% methanol, %5 acetic acid.
1×10 minutes in 50% methanol
1×10 minutes in dH2O water
1×1 minute in 0.02% Sodium-thiosulfate
3×2 minutes in dH2O
1×30 minutes in cold (4° C.) 0.1% silver nitrate
3×2 minutes in dH2O
1×1-10 minutes in 0.04% formaldhyde, 2% Sodium Carbonate with shaking
1×5 minutes in 5% acetic acid
Store gels in 1% acetic acid at 4 C protected from light.

Gel Analysis:

Gels were then scanned directly into the Z3 2Dgel analyses program using an UMAX MirageII scanner in transmissive mode. After analysis spots of interest were excised from the analytical gel, lypholized, and sent for mass spectrometric identification.

Northern Analysis

Preparation of RNA

E. coli λRTLF cells containing pTrpRep(T44M) and pPep (MGFLR) were grown in BTTRA and BTTRG media with, or without tryptophan, at 30° C. with shaking until OD 0.6 wavelength 600 was reached. A second E. coli λRTLF culture containing pTrpRep(WT) was grown in BTTRG culture at 30° C. with shaking until OD 0.6 wavelength 600 was reached.

Five ml of boiling lysis solution (Table 3) in a 50 ml conical tube (Falcon/Corning), was placed in a 100° C. water bath and incubated for 10 minutes. Ten ml of each culture was mixed with the boiling lysis solution and incubated at 100° C. for 5 minutes with periodic mixing. Ten ml of hot acid (65° C.) phenol/chloroform was added to each tube and the tubes sealed by adding parafin oil to prevent phenol evaporation. Samples were mixed well by vortexing at high speed. Samples were further incubated for 10 minutes at 65° C. with periodic mixing. Samples were spun for 15 min at 2500 g (approximately 3000 rpm in a Sorval RC3B rotor). The aqueous phase was carefully transferred (care was taken to avoid any of the white interface) to fresh 50 ml tube and an equal volume acid phenol/chloroform was added. The tube was sealed and mixed thoroughly by vortexing at high speed. Samples were then spun 3000 rpm 15 min. (~2500 g). Again the aqueous phase was transferred to a fresh 50 ml conical and an equal volume of chloroform/isoamyl alcohol was added. The tube was sealed and mixed well by vortexing. After spinning for 15 minutes at 3000 rpm, the aqueous phase was transferred to new 30 ml corex tube. Two volumes of 100% ethanol were added and 5M sodium acetate was added to a final concentration of 0.3M. Samples were stored at –20° C. overnight. Samples were then spun for 20 minutes at 15-20, 000 g (12,500 rpm in SS34 rotor). The supernatant was carefully poured off and the pellet washed with 5 ml of ice cold 70% EtOH (prepared with DEPC-H2O) and re-centrifuged as above. The pellet was dried at room temp for 20 minutes and resuspended in TE buffer made with DEPC treated $H_2O$.

DNA Hybridization Probe:

E. coli genomic DNA was extracted using a standard procedures and used as a template for the following PCR reactions. Primers pairs Amp forward, reverse, LacZ forward, reverse, and PheS forward, reverse were used in the following PCR reaction. PCR reaction: forward and reverse primers 20 mm, template 500 ng, $MgCl_2$ 3 mM, dNTP 0.2 mM, 1 unit pfu turbo, 5 μl 10× reaction buffer, and $dH_2O$ to total 50 μl. The lacZ PCR product was restricted with HindIII and filled with T4-DNA polymerase within the same reaction as suggested by the manufacturers instructions. Radioactively labeled α-P32 dCTP was substituted for dCTP in the fill in reaction. Likewise the pheS PCR product was restricted with PstI and T4 filled substituting -P32 radioactive dCTP for dCTP. Finally the Amp PCR product was restricted with enzyme BanI and T4 filled substituting radioactive α-P32 dCTP for dCTP. All cut and labeled PCR products were gel purified using Qia quick PCR clean up kit.

Hybridization and Analysis

RNA was electophoresed through a 1% formaldehyde gel according to Sambrooke et al's Manual (1989). The gel was capillary blotted onto nitrocellulose filter paper using the standard protocols. RNA was UV crosslinked by 45 seconds of UV exposure. The filter was prehydridised for 3 hours at 65 C and then hybridised for 36 hours at 65° C. Hybridisation buffers were in accordance with Sambrook. The filter was dried at room temperature and placed in a phosphoimager cassette overnight. The filter was then scanned by Molecular Dynamics phosphoimager 400e (880 E. Argues Ave, Sunnyvale Calif. 94086).

Results and Discussion:

An alanine to glycine substitution at position 294 (A294G) of the phenylalanyl-tRNA synthase (PheS) gene relaxes the specificity of the enzyme allowing the binding of DL-p-Cl-phenylalanine. The subsequent incorporation of DL-p-Cl-phenylalanine into the nascent peptide chain interferes with polypeptide folding and elongation resulting in cell death, a demonstration of an effective positive selection system.

Figure 10:
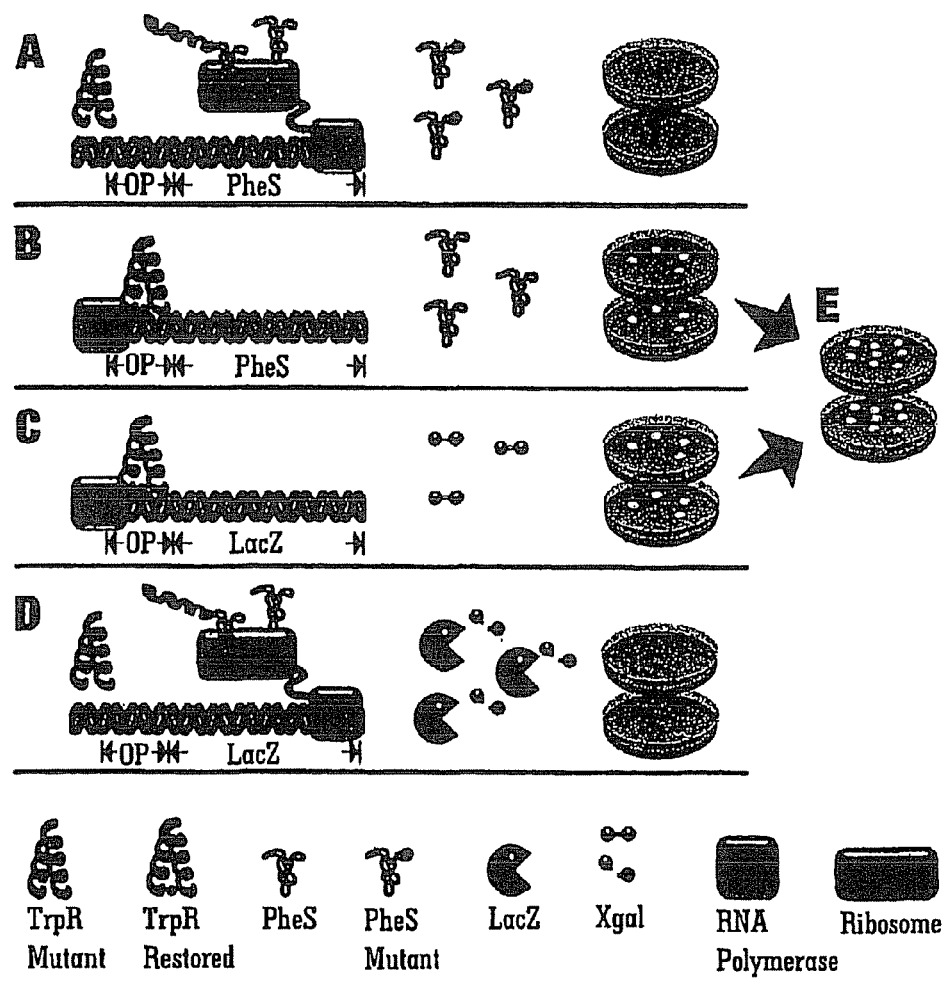

Since we have placed the PheS gene under the transcriptional control of TrpR, the binding of TrpR wildtype, or a restored TrpR mutant, to the TrpEDCBA operator rendered the cell immune to DL-p-Cl-phenylalanine by blocking transcription of PheS gene (Table 4). FIG. 10 shows the dual selection system with 2A and 2B showing PheS based selection. Colonies that falsely passed selection (Table 4) did not survive re-plating on fresh selective media.

The second reporter where the β-galactosidase (LacZ) gene was placed under the transcriptional control of TrpEDCBA operator promoter proved to be an invaluable confirmatory reporter. The LacZ gene cleaves the glycosidic linkage in X-gal to eventually produce the halogenated insoluble blue compound indigo in cells expressing LacZ. The E. coli cell line λRTLF has the TrpEDCBA operator-promoter placed in front of the lacZ gene to regulate expression but tryptophan synthesis remains unaffected. Binding of TrpR, or restored TrpR mutant to the TrpEDCBA operator prevents transcription of LacZ and results in a white colony phenotype. However, many colonies surviving PheS selection were blue in color, suggesting false restoration of the TrpR(T44M) mutant, and were eliminated as potential restoring peptides. The initial selection (Table 5) showed 150 surviving colonies of which 134 were white in color. The plasmids from these 134 colonies were isolated and plated on to fresh selective plates. Only 18 of the original 134 colonies flourished on new selective media, the rest either died or were blue in color. Of the 18 colonies that tolerated DL-p-Cl-phenylalanine in the media only three gave reliable sequencing results. The results are shown in Table 6. Peptides MGFLR, and MGFWR were deduced from the DNA sequences of the three positive sequencing results.

To determine the extent of TrpR(T44M) restoration and tryptophan dependence, b-galactosidase activity values were calculated in the presence of peptide-expressing plasmids. Results showed that other than the positive control pTrpRep (WT), only the arabinose induced peptide sequences MGFLR and MGFWR expressed from pPep(MGFLR)/pPep(MGFWR) plasmid restored TrpR(T44M) function. The same peptides did not restore the function of another TrpR mutant G85E.

Tri and pentameric polypeptides were synthesized from the isolated peptide sequence (Table 6). Likewise, the synthetic peptides were added to the media to determine the exact level of TrpR(T44M) restoration, through β-galactosidase reporter activity. The addition of 1 mM amounts of peptides (FWR, FLR) significantly reduced the expression of betagalactosidase from over 6,000 units to under 1000 units. Consistent with peptide expression from pPepLib the synthetic peptides failed to restore function of the G85E TrpR mutant. The longer pentameric synthetic peptides failed to restore the function of either TrpR mutant, G85E or T44M.

The functional restoration of TrpR(T44M) was not dependent on tryptophan in the media. -Galactosidase values were unaffected by the presence or absence of tryptophan for both pPep(MGFLR) and pPep(MGFWR). Only the plasmid pTrpRep(WT) was affected by the absence of tryptophan. In this case repression was slightly relieved.

The arabinose induced expression of peptide MGFLR from plasmid pPep(MGFLR) repressed the transcription of LacZ, and PheS, both in the presence and absence of tryptophan. The same plasmid could not repress transcription of LacZ or PheS in the presence of glucose. The control band β-lactamase remained constant and unaffected in all cases. The positive control TrpRep(WT) repressed the transcription of both LacZ and PheS.

A comparison was made of E. coli λRTLF cells containing the TrpRep(T44M) plasmid and one of pPep(MGFWR) or pBAD33. 2DPAGE revealed a spot which is present in the pBAD33 sample but not the pPep(MGFWR) sample. Mass spectrometry identified the spot as PheS, producing 10 different peptide fragments, all of which mapped to the PheS protein.

TABLE 4

Verification of the reporter system

|      |                      | None                                    | Tryptophan                              |
|------|----------------------|-----------------------------------------|-----------------------------------------|
| T44M | None                 | Positive control Colonies: ~10,000      | Positive control Colonies: ~10,000      |
|      | DL-Cl-phenyl-Alanine | Negative control Colonies: 20           | Negative control Colonies: 20           |
| WT   | None                 | Positive control Colonies: ~10,000      | Positive control Colonies: ~10,000      |
|      | DL-Cl-phenyl-Alanine | Negative control Colonies: 4-500        | Experimental Colonies: 5,000-6,000      |

TABLE 5

Selection of Restoring Peptide:

|      |                      | pBAD33 | | PPepLib | |
|------|----------------------|--------|--------|--------|--------|
|      |                      | Arabinose | Glucose | Arabinose | Glucose |
| T44M | None                 | Positive control Colonies: ~10,000 | Positive control Colonies: ~10,000 | Positive control Colonies: ~10,000 | Positive control Colonies: ~10,000 |
|      | DL-Cl-phenyl-Alanine | Negative control Colonies: 20 | Negative control Colonies: 20 | Experimental Colonies: 150 | Negative control Colonies: 20 |
| WT   | None                 | Positive control Colonies: ~10,000 | Positive control Colonies: ~10,000 | Positive control Colonies: ~10,000 | Positive control Colonies: ~10,000 |
|      | DL-Cl-phenyl-Alanine | Positive control Colonies: 5-6,000 | Positive control Colonies: 5-6,000 | Positive control Colonies: 5-6,000 | Positive control Colonies: 5-6,000 |

TABLE 6

Sequencing results of selected pPepLib vectors

| | | | |
|---|---|---|---|
| 01 | ~~~~~ ATGGGTTTTTGGAGGTGATAA ~~~~~ | (SEQ. ID. NO. : | 39) |
| 01 | ~~~~~ MetGlyPheLeuArgStpStp ~~~~~ | (SEQ. ID. NO. : | 40) |
| 10 | ~~~~~ ATGGGTTTTTGGAGGTGATAA ~~~~~ | (SEQ. ID. NO. : | 39) |
| 10 | ~~~~~ MetGlyPheLeuArgStpStp ~~~~~ | (SEQ. ID. NO. : | 40) |
| 11 | ~~~~~ ATGGGTTTTTGGAGGTGATAA ~~~~~ | (SEQ. ID. NO. : | 39) |
| 11 | ~~~~~ MetGlyPheTrpArgStpStp ~~~~~ | (SEQ. ID. NO. : | 41) |

Our experimentation strongly suggests that the function of TrpR (T44M) has been restored. Firstly the restoration is specific since the expressed peptide restored only the function of TrpR (T44M) and not that of TrpR (G85E) as judged by regulation of -galactosidase reporter activity. Therefore, the peptide is not simply mimicking TrpR function, but somehow interacts specifically with TrpR (T44M) to restore function. Secondly, the regulation of two unlinked reporter systems suggests that the TrpR (T44M) is indeed binding to the TrpEDCBA operator fragment. Lastly, the addition of synthesized peptides identical in sequence to peptides expressed from pPepLib had an effect on reporter system regulation, suggesting that the peptide, and not the pPepLib plasmid is responsible for the regulation of reporter system expression. In no case was the wild type TrpR protein affected by the addition of peptide.

The fact that the tri-peptides (FLR, FWR) had a greater effect on the regulation of the TrpEDCBA linked genes lacZ and pheS, than penta-peptides may be due to increased uptake than that of the larger penta-peptides across the membrane. In support of the above argument the expression of plasmid encoded pentameric peptides did have a dramatic effect on the expression of lacZ and pheS.

The two dimensional poly acrylamide electrophoresis technique gives an in vivo representation of protein expression. The presence, location, and amount of reporter protein pheS could be determined using 2DPAGE analysis. Restoration of the TrpRT44M protein leads to reduced expression of the TrpEDCBA regulating PheS. The reduction in expressed PheS could be clearly seen using the 2DPAGE technique. Other than the reduction of PheS expression, there were few differences between control (pBAD33) protein sample and experimental (MGFLR) sample on the gels. These results argue that the function of TrpR(T44M) has indeed been restored and that the TrpR(T44M) protein is relatively specific in its choice of the TrpEDCBA binding sites.

EXAMPLE 7

Protocol for Generation of Peptide Expression Libraries (Microgenex Libraries)

Materials and Methods:

1—Primers

Primers: Primers used to construct Microgenex libraries.

| No | Name | Sequence | bases |
|---|---|---|---|
| 1 | Master | AAGAGCTCGGTACCAAGAAGGAGTTTACATAT GGGANNKNNKNNKTGATAAGGATCCAAGCTTG AATTCAG (SEQ. ID. NO.: 42) | 71 |
| 2 | Left | AAGAGCTCGGTACCAAGAAGGAG (SEQ. ID. NO.: 43) | 23 |
| 3 | Right | CTGAATTCAAGCTTGGATCCTTATC (SEQ. ID. NO.: 44) | 25 |

The Sequencing primers used for the Microgenex verifications.

| No | Name | Sequence | bases |
|---|---|---|---|
| 1 | pCEP-f | AGAGCTCGTTTAGTGAACCG (SEQ. ID. NO.: 45) | 20 |
| 2 | pCEP-r | GTGGTTTGTCCAAACTCATC (SEQ. ID. NO.: 46) | 20 |
| 3 | Left* | AAGAGCTCGGTACCAAGAAGGAG (SEQ. ID. NO.: 47) | 23 |
| 4 | Right* | CTGAATTCAAGCTTGGATCCTTATC (SEQ. ID. NO.: 48) | 25 |

*These primers can also be used to verify sequence of any Microgenex. Other primers within the used cloning vector can also be used..

2—Cloning Vectors/Plasmids pCEP4 (Invitrogen): for mammalian expression.

pBAD33 (Dr. Beckwith, Harvard; Guzman et al., 1995 J. Bacteriol. 177 (14), 4121-4130) for *Escherichia coli* expression.

3—*Escherichia coli* strain used for Transforming Constructed Microgenex Libraries:

The Electrocompetent DH10B™ (Life Technologies, GibcoBRL) was used to transform the ligated Microgenex expression libraries.

4—PCR Conditions for Microgenex Amplifications 4.1. Concentrations of Primers:

| | |
|---|---|
| Master primer | 25 PM |
| Right primer | 100 PM |
| Left primer | 100 PM |

4.2. PCR Reactions:

At least two different Polymerases gave good results: Taq polymerase (Life Technologies, GibcoBRL) and rTth DNA polymerase (Perkin Elmer).

4.2.1. Standard Taq Polymerase as for Example in SuperMix (Life Technologies, GibcoBRL).

Prepare 1 to 10 PCR tubes with the following:

90 μl SuperMix

2 μl Master Primer (25 PM)

4 µl Right Primer (100 PM)
1 Left Primer (100 PM)
4.2.2 The XL PCR, Extra Long (rTth DNA Polymerase) (Perkin Elmer)

Also this PCR polymerase worked very well after adding buffers according to the manufacturer, but using primers as above and also the PCR cycles as indicated below.

4.2.3. PCR Cycles

Best Conditions were found by making a hot start at 95 for 3-5 minutes. PCR cycles were preformed only using 25 cycles. Example for PCR Cycle:

| Hot start | 95° C. | 3 min. |
|---|---|---|
| 25 cycles | | |
| Denaturation | 94° C. | 1 min. |
| Aneaing | 38° C. | 1 min. |
| Elongation | 60° C. | 1 min. |
| Hold at | 4° C. | |

5. Ligation of PCR Products to the Corresponding Expression Vector:

PCR product was first treated with phenol-chloroform, chloroform and then precipitated with 3 volumes of cold ethanol. The DNA pellet was washed with cold 70% ethanol, dried and dissolved in appropriate volume of $H_2O$. DNA was then restricted by KpnI and HindIII. Restricted DNA was gel-purified and subsequently ligated to the corresponding expression vector that has been also restricted with by KpnI and HindIII. Ligation mix was precipitated and resuspended in $H_2O$ and subsequently used to transform, by electroporation, of the *Escherichia coli* strain DH10B™ (Life Technologies, GibcoBRL). Plating was done on LB ampicilin plates (200 µg/ml) for pCEP4, or chloramphenicol (40 µg/ml) for pBAD33.

6. Pooling of Colonies:

Colonies from all the plates were pooled together, washed with LB with ampicilin (200 µg/ml) if the cloning vector contains beta-lactamase gene, such in the case of pCEP4. This step is important to get rid of cells that lack the plasmid. Pooled cell mixture was divided into small aliquots and stored at −70° C. Each aliquot contained millions of cells to ensure complexity of the Microgenex library.

7. DNA Isolation of Microgenex Library:

One frozen portion can be used to inoculate a one-liter culture of LB containing the appropriate antibiotic. Standard plasmid DNA isolation protocols/kits are used to isolate the DNA suitable to transform, for example mammalian cells for ligand screening.

Master primer was used as a template for all constructed peptide expression libraries (Microgenex) whether the expression in mammalian cells or *Escherichia coli*. It could also be used for yeast or insect cell expression. Left and Right oligos were used as forward and reverse primers, in order to generate double-stranded DNA fragments encoding repertoire of peptide library by PCR. The first ATG in this fragment encodes Met as the translation initiation site of the peptides. Gly, the second amino acid encoding by the DNA fragment, assures the peptides expressed to be stable inside cells according to the N-end rule. The following three repeats of NNK code (N for A, C, G, and T in equal molar ratio, K for G and T in equal molar ratio) for all possible amino acids thus form the peptide library. Two stop codons, TGA and TAA, are added right after the last NNK to stop peptide translation. The 5'-end KpnI site and 3'-end HindIII allows the fragments to be cloned into pCEP4 vector in the correct direction under CMV promoter.

The peptide-coding DNA-fragment was inserted into the mammalian expression vector pCEP4 between its KpnI and HindIII site under the CMV promoter. The plasmid has the replication origin, OriP, which enables the replication of the plasmid inside mammalian cells. Selection marker expression cassette in the plasmid provides the plasmid-transfected cells with hygromycin resistance.

After ligation of the KpnI/HindIII restricted PCR product, and the KpnI/HindIII restricted pCEP4 or pBAD 33, the DNA were electroporated into DH10B™ (Life Technologies, GibcoBRL) cells. Transformants were plated on LB plates with ampicilin (200 µg/ml) or Chloramphenicol (40 µg/ml) depending on the coloning vector used in the construction of the Microgenex library. All colonies from all the plates were pooled together, washed with LB with ampicilin (200 µg/ml), only if the cloning vector contains beta-lactamase gene, such in the case of pCEP4. Pooled cell mixture was divided into small aliquots and stored at −70° C. Each frozen portion of the Microgenex library can be used to inoculate and start a 1-liter-culture (with the appropriate antibiotic, in order to prepare the plasmid DNA. Insertions were verified by PCR of the generated Microgenex with Right and Left oligoes. Also, the forward and reverse primers of pCEP4 were used for verifications for the constructed mammalian Microgenex. Similar PCR reactions were preformed using plasmid DNA prepared from a small number of randomly-picked colonies in order to estimate the cloning efficiency and the ratio of peptide-encoding plasmids to empty vectors in any given Microgenex. Note that all generated peptides will start with M and G amino acids followed by three random amino acids (X, X, X) It should be noted that the number of the random amino acids (X) can be changed by changing the number of the codes (NNK).

EXAMPLE 8

Dose Response and Cytotoxicity of Synthesized Ligands Using the Metastatic Cancer Cell Line SW480 and Normal Human Lymphocytes SW480 cells have a mutant and less active form of p53. It has been shown that introduction of wild type p53 results in SW480 cell death. Peptides identified as able to restore p53 wild type function have been tested for their ability to reduce the number of SW480 cells present in a sample i.e. cause cell death, reduce rate of cell division etc.

Materials and Methods:
Drug-1: Folic-MGWCT. Folate was made at the N-end of the penta-peptide. (MW=1037.2)
Drug-2: MGWCT-K-Folic. Folate was made at the carboxyl end of the penta-peptide. (MW=1165.4)
Drug-3: MGWCT. No folate conjugation (MW=595.8)

All the peptide synthesis and purification were made (10-15 mg) by made via MedProbe (P.O. Box 2640, N-0131 Oslo Norway. Amino acid K was added as indicated to Drug2 to make the synthesis possible I—Dose Response in SW480
1. Dissolve the drug at a concentration of 10 mg/ml in PBS.
2. 100 l of a series of concentration of 1600, 800, 400, 200, 100, 50, 25, 12.5, 6.25 µg/ml were made. Triplicate wells were used for each concentration as well as the control (0.0 µg/ml), for each of Drug1, 2 and 3.
3. A confluent flask of SW480 cells was treated with trypsin and the cells were suspended in growth media at concentrations of $5 \times 10^5$ cells/ml.

4. Add 100 μl of cell suspension to each well to give a final concentration of 5×10⁴ cells/well. Thus giving final drug concentrations of 800, 400, 200, 100, 50, 25, 12.5, 6.25 and 3.125 μg/ml.

5. Incubate at 37° C., 5% $CO_2$ for 2 days.

II—Toxicity Test Using Isolated Normal Human Lymphocytes

Growth media used is the RPMI-1640 (Gibco Laboratories, Grand Island, N.Y.) supplemented with 25 mM Hepes buffer, 10% FBS serum (Gibco), 100 U/ml penicillin/streptomycin, 50 μg/ml gentamycin, 2 mM L-glutamin, 1× non-essential amino acids (Gibco)

RPMI-1640:

| | |
|---|---|
| Dry powder (Sigma R 6504) | 10.4 g |
| $NaHCO_3$ | 2 g |
| Penicillin and streptomycin (100 U/ml) | 5 ml |
| $H_2O$ | add to 1 L |

10× HBSS (Hanks balanced salt solution):

| | |
|---|---|
| NaCl | 76.5 g |
| KCl | 4 g |
| $Na_2HPO_4$ 12$H_2O$ | 1.2 g |
| $KH_2PO_4$ | 0.6 g |
| $H_2O$ | add to 1 L |

Lymphoprep™ was obtained from Axis-Shield ProC A/S, Oslo Norway Note that 1 ml of blood contains Total no. of cells: 5.1×10⁶ cells/ml
Lymphocytes: 1.8×10⁶ cells/ml
Mixed (monocytes and platelets) 0.9×10⁶ cells/ml
Red blood cells: 2.4×10⁶ cells/ml Procedure:

1. In a 50-ml centrifugation tube, add 10 ml of Lymphoprep™.
2. Mix 15 ml blood and 15 ml HBSS-buffer (containing heparin).
3. Carefully add the blood mixture from step 2, to the tubes containing Lymphoprep™ without mixing the phases.
4. Centrifuge at 450 g at room temperature for 45 min.
5. Isolate the Buffy-coat layer containing the PBMC (peripheral blood mononuclear cells), and place in a fresh tube.
6. Add 7 ml HBSS-buffer to the tube to wash the PBMC.
7. Centrifuge 5-10 min 600 g.
8. Remove the supernatant and wash the PBMC again with a total of 10-ml HBSS-.
9. Suspend the cells in complete media RPMI 1640. Incubate the cells in a small culture flask for 1 hour at 37° C.
10. Remove the unattached cells (lymphocytes) from the small culture flask and dilute the cells to a concentration of 5×10⁵ cell/ml.
11. Dissolve drug at 10 mg/ml in PBS.
12. Add 100 μl of growth media to the rest of the wells.
13. Prepare 100 l of a series of concentration of 1600, 800, 400, 200, 100, 50, 25, 12.5, 6.25 μg/ml were made. Triplicate wells were used for each concentration as well as the control (0.0 g/ml), for each of Drug1, 2 and 3.
14. Add 100 μl of cell suspension to each well to give a final concentration of 5×10⁴ cells/well. Thus giving final drug concentrations of 800, 400, 200, 100, 50, 25, 12.5, 6.25 and 3.125 g/ml.
15. Incubate at 37° C., 5% $CO_2$ for 2 days.

Results

Figure 11:
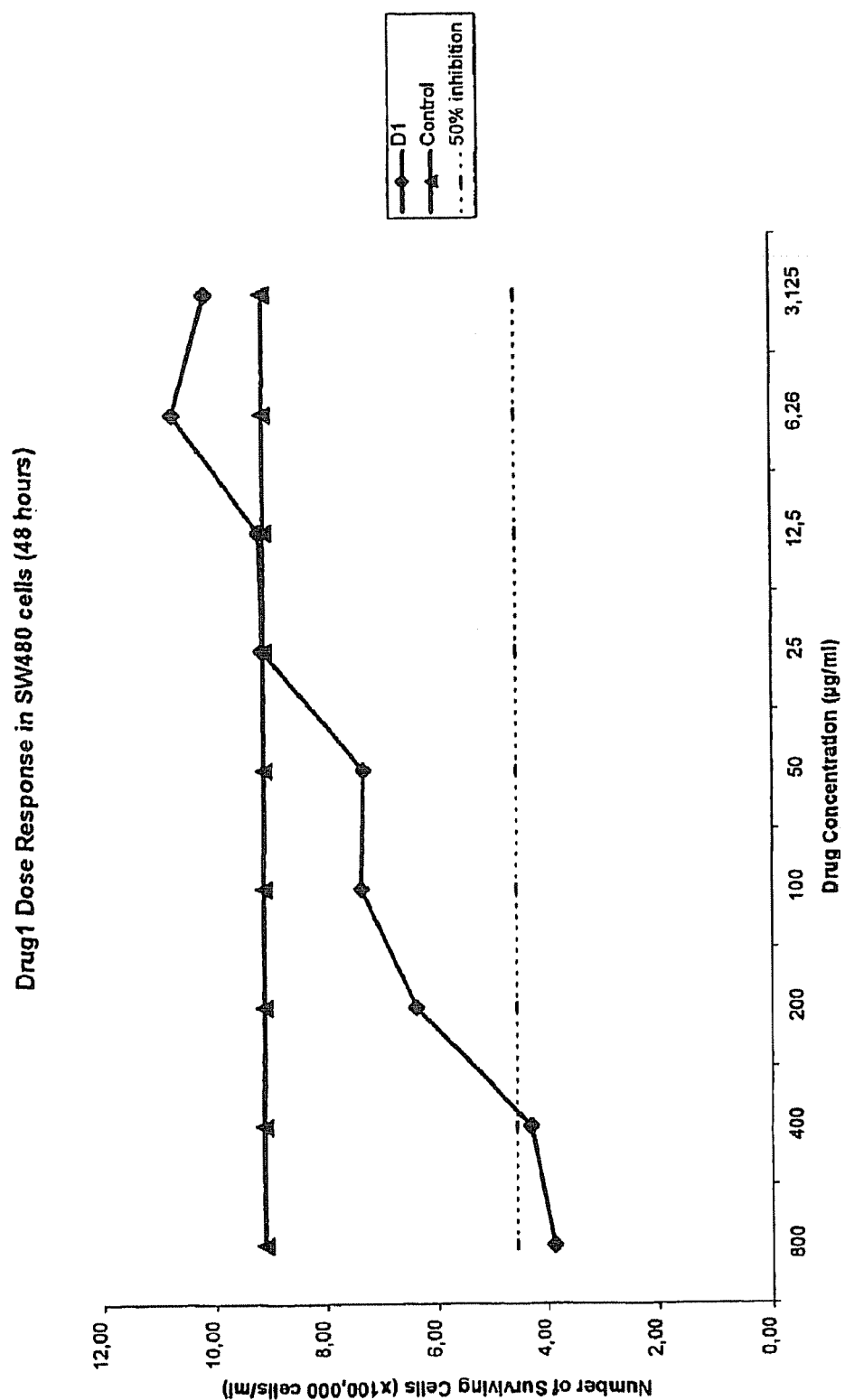
FIG. 11 shows the number of surviving SW480 cells following administration of various doses of Drug 1 and a control, as described in Example 8.
Figure 12:
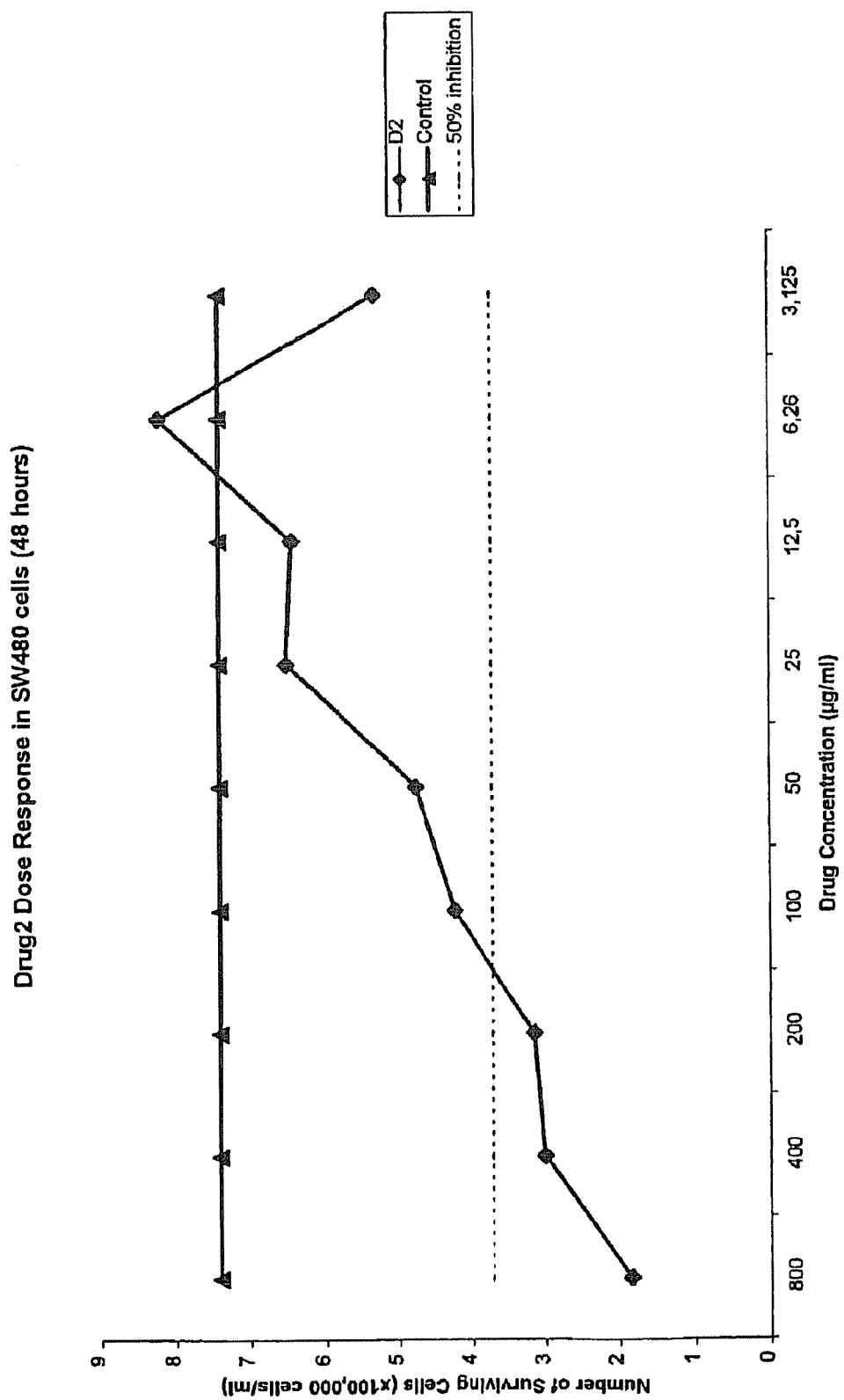
FIG. 12 shows the number of surviving SW480 cells following administration of various doses of Drug 2 and a control, as described in Example 8.
Figure 13:
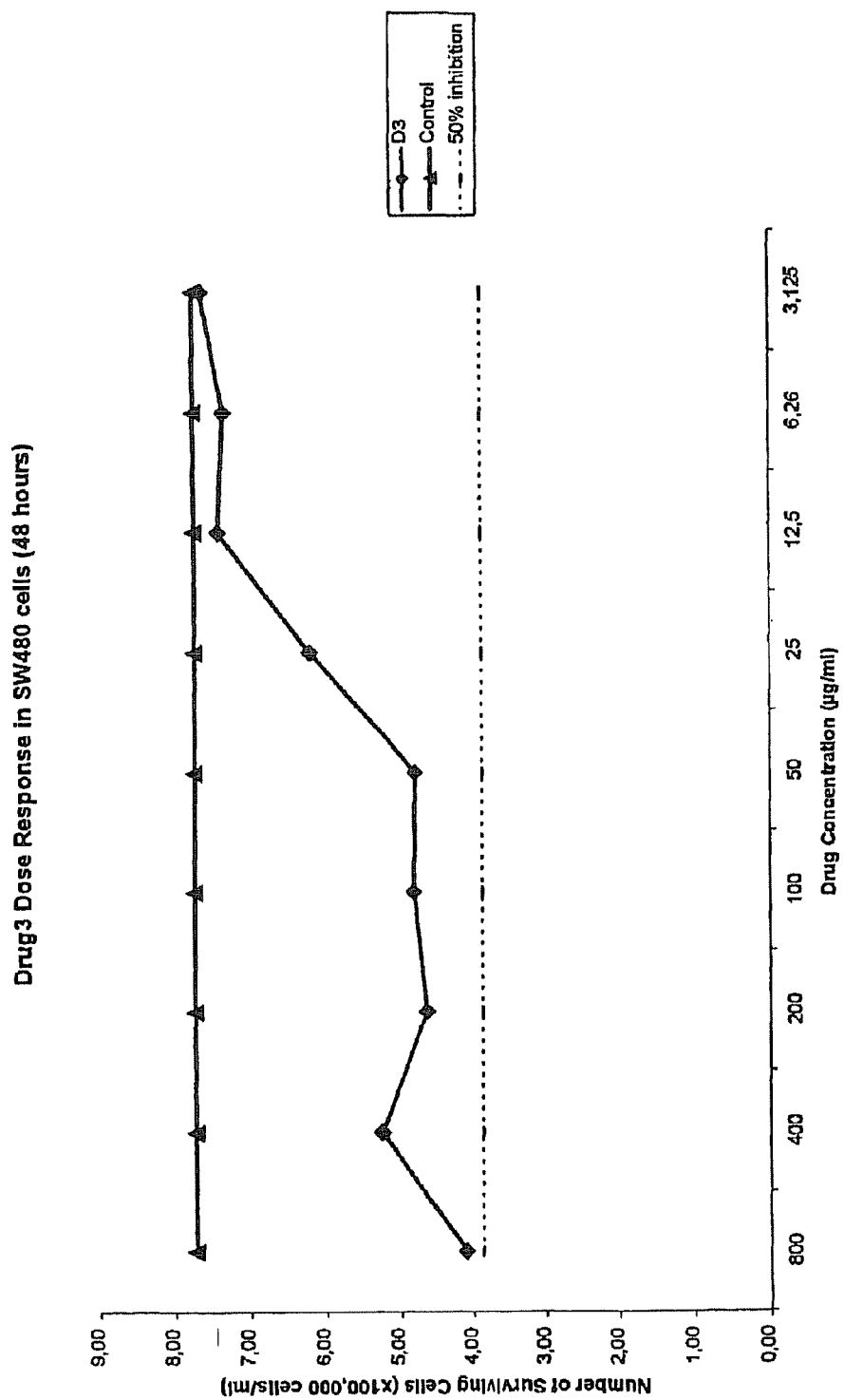
FIG. 13 shows the number of surviving SW480 cells following administration of various doses of Drug 3 and a control, as described in Example 8.

Drug 2 gave the best results among the three different fowls tested on the mestataic cancer cells SW480 but all showed strong activity, see FIGS. 11 to 13.

It should be noted that molecular weight of drug 2 is nearly double that of drug 3 due both the addition of K and folate. But the IC50 was only 150 μg/ml. That is 30 g/well amounting to only 0.0257 μmol/well.

Figure 14:
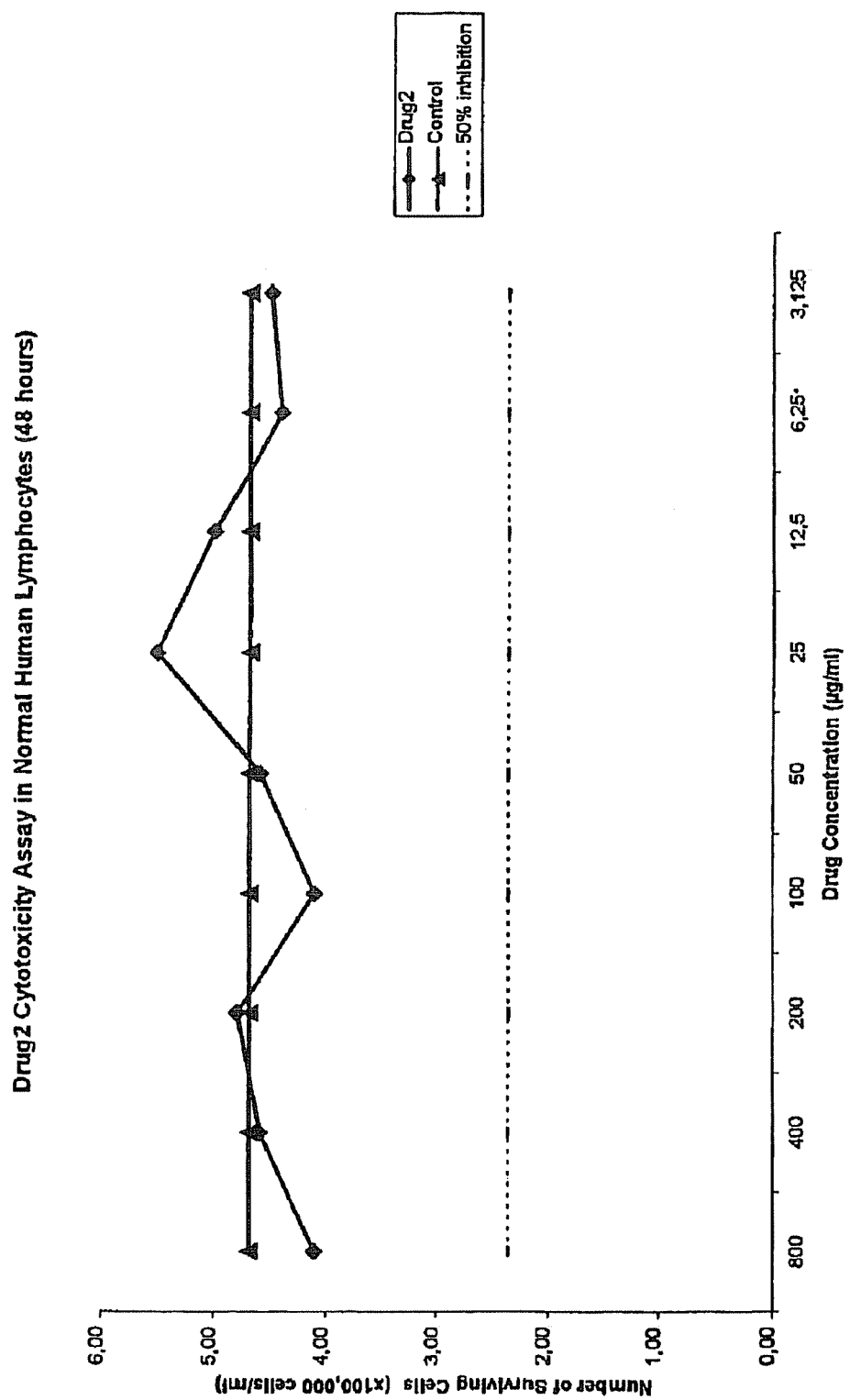
FIG. 14 shows the number of surviving normal human lymphocytes following administration of various doses of Drug 2 and a control, as described in Example 8.

The results also demonstrated (FIG. 14) that Drug 2 has no effect on normal human lymphocytes. This again confirms the fact that the ligand has no toxic effect on normal cells, that is cells that have no mutations in p53.

Anfinsen C. (1986) Protein Engineering Ed. Inouye and Sarma pp 3-13.

Blin N., and Stafford D. W. A general method for isolation of high molecular weight DNA from eukaryotes. *Nucleic Acids Research* 1976, 3:2303-2308.

Colas P., Cohen B., Jessen T., Grishina I., McCoy J., and Brent R. Genetic selection of peptide aptamers that recognize and inhibit cyclin-dependent kinase 2. *Nature* 1996, 380:548-550.

El-Deiry W. S., Tokino T., Velculescu V. E., Levy D. B., Parsons R., Trent J. M., Lin D., Mercer W. E., Kinzler K. W., and Vogelstein B. WAF1, a potential mediator of p53 tumor suppression. *Cell* 1993, 75:817-825.

El-Gewely, M. R. Shorter is better. Nature Biotechnology 1999, 17: 210.

Fenton C., Hansen A., and El-Gewely M. R. Modulation of the *Escherichia coli* tryptophan repressor protein by engineered peptides. *Biochem Biophys Res Commun* 1998, 242: 71-78.

Foster B A, Coffey H A, Morin M J, Rastinejad F. 1999. Pharmacological rescue of mutant p53 conformation and function. Science; 286(5449):2507-10.

Fukazawa T., Fujiwara T., Morimoto Y., Shao J., Nishizaki M., Kadowaki Y., Hizuta A., Owen-Schaub L. B., Roth J. A., and Tanaka N. Differential involvement of the CD95 (Fas/APO-1) receptor/ligand system on apoptosis induced by the wild-type p53 gene transfer in human cancer cells. *Oncogene* 1999, 18:2189-2199.

Gates C. M., Stemmer W. P. C., Kaptein R., and Schatz P. J. Affinity selective isolation of ligands from peptide libraries through display on a lac repressor "headpiece dimer". *J Mol Biol* 1996, 255:373-386.

Hanes J., and Plückthun A. In vitro selection and evolution of functional proteins by using ribosome display. *Proc Natl Acad Sci USA* 1997, 94:4937-4942.

Harayama S. Artificial evolution by DNA shuffling. *Trends Biotechnol* 1998,16:76-82.

Hermeking H., Lengauer C., Polyak K., He T. C., Zhang L., Thiagalingam S., Kinzler K. W., and Vogelstein B. 14-3-3 sigma is a p53-regulated inhibitor of G2/M progression. *Mol Cell* 1997, 1:3-11.

Kim A L, Raffo A J, Brandt-Rauf P W, Pincus M R, Monaco R, Abarzua P, Fine R L. 1999. Conformational and molecular basis for induction of apoptosis by a p53 C-terminal peptide in human cancer cells. J Biol Chem 274(49):34924-31.

Lowman H. B. Bacteriophage display and discovery of peptide leads for drug development. *Annu Rev Biophys Biomol Struct* 1997, 26:401-424.

Parker B. A., and Stark G. R. Regulation of simian virus 40 transcription: sensitive analysis of the RNA species present early in infections by virus or viral DNA. *J Virol* 1979, 31:360-369.

Selivanova G., Ryabchenko L., Jansson E., Iotsova V., and Wiman K. G. Reactivation of mutant p53 through interaction of a C-terminal peptide with the core domain. *Mol Cell Biol* 1999, 19:3395-3402.

Sigal A., and Rotter V. Oncogenic mutations of the p53 tumor suppressor: the demons of the guardian of the genome. *Cancer Res* 2000, 60:6788-6793.

Storbakk, N., Fenton C., Frostad Riise, H. M., Nilsen, I. and El-Gewely, M. R. In vivo interaction between mutated tryptophan repressors of *Escherichia coli*. Journal of Molecular Biology. 1996, Vol. 256: 889-896.

Thornborrow E. C., and Manfredi J. J. One mechanism for cell type-specific regulation of the bax promoter by the tumor suppressor p53 is dictated by the p53 response element. *J Biol Chem* 1999, 274:33747-3356.

Varshavsky A. The N-end rule pathway of protein degradation. *Genes Cells* 1997, 2:13-28.

Vogelstein B., Lane D., and Levine A. J. Surfing the p53 network. *Nature* 2000, 408:307-310.

Watanabe T, Sullenger B A. 2000. Induction of wild-type p53 activity in human cancer cells by ribozymes that repair mutant p53 transcripts. Proc Natl Acad Sci USA; 97(15): 8490-4.

Wolff R. A., and Hull R. A rapid and easy method for DNA recovery from agarose gels using Wizard minicolumns. *Trends Genet* 1996, 12:339-340.

Xu, H., El-Gewely, M. R. 2001. P53-responsive genes and the potential for cancer diagnostics and therapeutics development. Review. in Biotechnology Annual Review, edited by M. R. El-Gewely, pages 131-164 (Vol 7). Elsevier. Amsterdam.

Yu J., Zhang L., Hwang P. M., Rago C., Kinzler K. W., and Vogelstein B. Identification and classification of p53-regulated genes. *Proc Natl Acad Sci USA* 1999, 96:14517-14522.

The invention claimed is:

1. A method of restoring wild-type function of mutant human p53 comprising contacting a cell having the mutant human p53 with a peptide of 3-7 amino acids, wherein the sequence of the mutant human p53 includes mutations R273H and P309S as compared to the wild-type human p53, and wherein the peptide of 3-7 amino acids incorporates tri-peptide sequence WCT.

2. The method of claim 1, wherein the peptide incorporates a modification of at least one of the N-terminal amino acid and the C-terminal amino acid.

3. The method of claim 1, wherein the peptide has 3-5 amino acids.

4. The method of claim 1, wherein the peptide has the sequence of SEQ ID NO: 51.

5. The method of claim 1, wherein the peptide has the sequence of SEQ ID NO: 3.

6. The method of claim 1, wherein the peptide is selected from the group consisting of folate-MGWCT (SEQ ID NO: 3), MGWCT-K-folate (SEO ID NO: 52), Acetyl-MGWCT-amide-folate (SEQ ID NO: 3), Acetyl-WCT-amide-folate, Acetyl-MGWCT-amine-Tat (SEQ ID NO: 3), Folate-WCT, Folate-WCT-amide and Acetyl-WCT-K-folate (SEQ ID NO: 53).

* * * * *